United States Patent
Chapman et al.

(10) Patent No.: US 8,834,350 B2
(45) Date of Patent: Sep. 16, 2014

(54) SURGICAL IMPLANTS, TOOLS, AND METHODS FOR TREATING PELVIC CONDITIONS

(75) Inventors: Kelly Ann Chapman, Minnetonka, MN (US); Richard Kaleta, Minnetonka, MN (US); Chaouki A. Khamis, Minnetonka, MN (US); Karen Pilney Montpetit, Minnetonka, MN (US); Jason Ogdahl, Minnetonka, MN (US); Jeffrey Michael O'Hern, Minnetonka, MN (US); John F. Otte, Minnetonka, MN (US); Jessica L. Roll, Minnetonka, MN (US); Steven James Wolfe, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 1673 days.

(21) Appl. No.: 12/308,436

(22) PCT Filed: Jun. 15, 2007

(86) PCT No.: PCT/US2007/014120
§ 371 (c)(1),
(2), (4) Date: Oct. 29, 2010

(87) PCT Pub. No.: WO2007/149348
PCT Pub. Date: Dec. 27, 2007

(65) Prior Publication Data
US 2011/0112357 A1 May 12, 2011

Related U.S. Application Data

(60) Provisional application No. 60/805,040, filed on Jun. 16, 2006, provisional application No. 60/897,697, filed on Jan. 26, 2007, provisional application No. 60/863,055, filed on Oct. 26, 2006.

(51) Int. Cl.
*A61F 2/00* (2006.01)
*A61F 13/00* (2006.01)
(Continued)

(52) U.S. Cl.
CPC ......... *A61F 2/0045* (2013.01); *A61B 17/06109* (2013.01); *A61B 2017/0437* (2013.01); *A61B 2017/06019* (2013.01); *A61B 2017/06176* (2013.01); *A61B 201/0435* (2013.01); *A61B 2017/06009* (2013.01); *A61F 2250/0004* (2013.01); *A61B 2017/0412* (2013.01); *A61B 2017/0488* (2013.01); *A61B 201/00805* (2013.01); *A61F 2002/30537* (2013.01); *A61B 17/064* (2013.01); *A61B 17/0401* (2013.01); *A61B 17/068* (2013.01); *A61B 2017/06042* (2013.01)
USPC ............................................. 600/37; 600/29

(58) Field of Classification Search
USPC ...................................................... 600/37, 29
See application file for complete search history.

(56) References Cited

U.S. PATENT DOCUMENTS 2,738,790 A   3/1956   Todt et al.
(Continued)

FOREIGN PATENT DOCUMENTS

AU   2002241673   11/2005
(Continued)

OTHER PUBLICATIONS

"We're staying ahead of the curve" Introducing the IVS Tunneller Device for Tension Free Procedures, Tyco Healthcare, 3 pages (2002).
(Continued)

*Primary Examiner* — Christine Matthews
*Assistant Examiner* — Sunita Reddy
(74) *Attorney, Agent, or Firm* — Kagan Binder, PLLC

(57) ABSTRACT

Described are pelvic implants (e.g., urinary incontinence sling, hammock, etc.) that provide treatment for pelvic floor disorders such as incontinence, stress urinary incontinence, prolapse (e.g., cystocele, enterocele, rectocele, vault prolapse), fecal incontinence, and the like, wherein the implant involves the ability to adjust dimensions of an implant before, during, or after implantation. In a preferred embodiment the implant (680) comprises a support portion piece (682) and an extension portion piece (688, 690) adjustably connected to the support portion piece through a frictional adjusting element (696) comprising an aperture through which a segment of extension portion extends.

9 Claims, 27 Drawing Sheets

(51) Int. Cl.
*A61B 17/06* (2006.01)
*A61B 17/04* (2006.01)
*A61F 2/30* (2006.01)
*A61B 17/064* (2006.01)
*A61B 17/068* (2006.01)

(56) References Cited

U.S. PATENT DOCUMENTS

| | | |
|---|---|---|
| 3,054,406 A | 9/1962 | Usher |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 4,979,956 A | 12/1990 | Silvestrini |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,203,864 A | 4/1993 | Phillips |
| 5,209,756 A | 5/1993 | Seedhom et al. |
| 5,234,438 A | 8/1993 | Semrad |
| 5,256,133 A | 10/1993 | Spitz |
| 5,268,001 A | 12/1993 | Nicholson et al. |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,354,292 A | 10/1994 | Braeuer et al. |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,439,467 A | 8/1995 | Benderev et al. |
| 5,474,518 A | 12/1995 | Farrer Velazquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,643,320 A | 7/1997 | Lower et al. |
| 5,647,836 A | 7/1997 | Blake et al. |
| 5,669,935 A | 9/1997 | Rosenman et al. |
| 5,674,247 A | 10/1997 | Sohn |
| 5,683,349 A | 11/1997 | Makower et al. |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonutti |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,873,891 A | 2/1999 | Sohn |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,007,539 A | 12/1999 | Kirsch et al. |
| 6,010,447 A | 1/2000 | Kardjian |
| 6,019,768 A | 2/2000 | Wenstrom et al. |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,074,341 A | 6/2000 | Anderson et al. |
| 6,077,216 A | 6/2000 | Benderev et al. |
| 6,099,538 A | 8/2000 | Moses et al. |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Rizvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |

(56) References Cited

U.S. PATENT DOCUMENTS

| | | |
|---|---|---|
| 6,319,272 B1 | 11/2001 | Brenneman et al. |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | Gellman et al. |
| 6,447,505 B2 | 9/2002 | McGovern et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin et al. |
| 6,635,058 B2 | 10/2003 | Beyar et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman |
| 6,691,711 B2 | 2/2004 | Raz et al. |
| 6,699,175 B2 | 3/2004 | Miller |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Pintauro et al. |
| 6,755,781 B2 | 6/2004 | Gellman |
| 6,802,807 B2 | 10/2004 | Anderson et al. |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning |
| 6,969,347 B2 | 11/2005 | Miller |
| 6,971,986 B2 | 12/2005 | Staskin et al. |
| 6,974,462 B2 | 12/2005 | Sater |
| 6,979,317 B2 | 12/2005 | Galt et al. |
| 6,981,944 B2 | 1/2006 | Jamiolkowski et al. |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin et al. |
| 7,025,772 B2 | 4/2006 | Gellman et al. |
| 7,037,255 B2 | 5/2006 | Inman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,059 B2 | 8/2006 | Harari et al. |
| 7,087,065 B2 | 8/2006 | Ulmsten et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,404 B2 | 6/2007 | Bouffier |
| 7,229,453 B2 | 6/2007 | Anderson et al. |
| 7,235,043 B2 | 6/2007 | Gellman et al. |
| 7,261,723 B2 | 8/2007 | Smith et al. |
| 7,267,645 B2 | 9/2007 | Anderson et al. |
| 7,273,448 B2 | 9/2007 | Siegel et al. |
| 7,291,104 B2 | 11/2007 | Neisz et al. |
| 7,297,102 B2 | 11/2007 | Smith et al. |
| 7,299,803 B2 | 11/2007 | Kovac et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,402,133 B2 | 7/2008 | Chu et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,431,690 B2 | 10/2008 | Merade et al. |
| 7,494,495 B2 | 2/2009 | Delorme et al. |
| 7,500,945 B2 | 3/2009 | Cox et al. |
| 7,513,865 B2 | 4/2009 | Bourne et al. |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,608,036 B2 | 10/2009 | Raz et al. |
| 7,611,454 B2 | 11/2009 | De Leval |
| 7,614,999 B2 | 11/2009 | Gellman et al. |
| 7,621,864 B2 | 11/2009 | Suslian et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff et al. |
| 7,753,839 B2 | 7/2010 | Siegel et al. |
| 7,762,942 B2 | 7/2010 | Neisz et al. |
| 7,762,969 B2 | 7/2010 | Gellman et al. |
| 7,766,926 B2 | 8/2010 | Bosley et al. |
| 7,789,821 B2 | 9/2010 | Browning |
| 7,794,385 B2 | 9/2010 | Rosenblatt |
| 7,828,715 B2 | 11/2010 | Haverfield |
| 2001/0000533 A1 | 4/2001 | Kovac |
| 2001/0018549 A1 | 8/2001 | Scetbon |
| 2001/0023356 A1 | 9/2001 | Raz et al. |
| 2001/0027321 A1 | 10/2001 | Gellman et al. |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0022841 A1 | 2/2002 | Kovac |

(56) References Cited

U.S. PATENT DOCUMENTS

| | | |
|---|---|---|
| 2002/0028980 A1 | 3/2002 | Thierfelder et al. |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyar |
| 2002/0095181 A1 | 7/2002 | Beyar |
| 2002/0099260 A1 | 7/2002 | Suslian et al. |
| 2002/0103542 A1 | 8/2002 | Bilbo |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0128681 A1 | 9/2002 | Broome et al. |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0188169 A1 | 12/2002 | Kammerer et al. |
| 2003/0004395 A1 | 1/2003 | Therin |
| 2003/0004581 A1 | 1/2003 | Rousseau |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0176875 A1 | 9/2003 | Anderson et al. |
| 2004/0015057 A1 | 1/2004 | Rocheleau et al. |
| 2004/0039453 A1 | 2/2004 | Anderson et al. |
| 2004/0073235 A1 | 4/2004 | Lund et al. |
| 2004/0116774 A1* | 6/2004 | Migliari ................. 600/37 |
| 2004/0193215 A1 | 9/2004 | Harari et al. |
| 2004/0215054 A1 | 10/2004 | Siegel et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt |
| 2006/0041185 A1* | 2/2006 | Browning ................. 600/37 |
| 2006/0058578 A1 | 3/2006 | Browning |
| 2006/0089524 A1 | 4/2006 | Chu |
| 2006/0089525 A1* | 4/2006 | Mamo et al. ............ 600/37 |
| 2006/0122457 A1 | 6/2006 | Kovac et al. |
| 2006/0173237 A1 | 8/2006 | Jacquetin |
| 2006/0195007 A1 | 8/2006 | Anderson et al. |
| 2006/0195011 A1 | 8/2006 | Arnal et al. |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0287571 A1 | 12/2006 | Gozzi et al. |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0182190 A1 | 7/2009 | Dann |
| 2009/0221867 A1 | 9/2009 | Ogdahl et al. |
| 2009/0221868 A1 | 9/2009 | Evans |
| 2009/0240102 A1 | 9/2009 | Rane et al. |
| 2009/0259092 A1 | 10/2009 | Ogdahl et al. |
| 2010/0010631 A1 | 1/2010 | Otte et al. |
| 2010/0094079 A1 | 4/2010 | Inman et al. |
| 2010/0152528 A1 | 6/2010 | Chapman et al. |
| 2010/0168505 A1 | 7/2010 | Inman et al. |
| 2010/0174134 A1 | 7/2010 | Anderson et al. |
| 2010/0261950 A1 | 10/2010 | Lund et al. |
| 2010/0261952 A1 | 10/2010 | Montpetit et al. |

FOREIGN PATENT DOCUMENTS

| | | |
|---|---|---|
| CA | 2404459 | 8/2005 |
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 0941712 A1 | 9/1999 |
| EP | 1093758 A1 | 4/2001 |
| EP | 1060714 A3 | 9/2002 |
| EP | 1342450 B1 | 9/2003 |
| EP | 1320336 B1 | 7/2005 |
| FR | 2787990 A1 | 7/2000 |
| FR | 2852813 A1 | 1/2004 |
| FR | 285817 | 10/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9310715 A1 | 6/1993 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO97630638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0030556 A1 | 6/2000 |
| WO | WO0040158 A2 | 7/2000 |
| WO | WO0057796 A1 | 10/2000 |
| WO | WO0057812 A1 | 10/2000 |
| WO | WO0060030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |

(56) References Cited

FOREIGN PATENT DOCUMENTS

| | | |
|---|---|---|
| WO | WO0139670 A1 | 6/2001 |
| WO | WO145588 A1 | 6/2001 |
| WO | WO0145589 A1 | 6/2001 |
| WO | WO0156499 A1 | 8/2001 |
| WO | WO0222184 A2 | 3/2002 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO02091950 A1 | 11/2002 |
| WO | WO03013392 A2 | 2/2003 |
| WO | WO03017848 A1 | 3/2003 |
| WO | WO03003778 A1 | 4/2003 |
| WO | WO03028585 A2 | 4/2003 |
| WO | WO03034891 A2 | 5/2003 |
| WO | WO03034939 A1 | 5/2003 |
| WO | WO03037215 A2 | 5/2003 |
| WO | WO03041613 A1 | 5/2003 |
| WO | WO03047435 A1 | 6/2003 |
| WO | WO03047476 A1 | 6/2003 |
| WO | WO03068107 A1 | 8/2003 |
| WO | WO03073960 A1 | 9/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2004041115 A1 | 5/2004 |
| WO | WO2004045457 A1 | 6/2004 |
| WO | WO2005004727 A1 | 1/2005 |
| WO | WO2005037132 A2 | 4/2005 |
| WO | WO2005046511 A2 | 5/2005 |
| WO | WO2005048850 A2 | 6/2005 |
| WO | WO2005079702 A1 | 9/2005 |
| WO | WO2005087153 A2 | 9/2005 |
| WO | WO2005094741 A1 | 10/2005 |
| WO | WO2005112842 A1 | 12/2005 |
| WO | WO2005122954 A1 | 12/2005 |
| WO | WO2006007189 A1 | 1/2006 |
| WO | WO2006007190 A1 | 1/2006 |
| WO | WO2006015031 A2 | 2/2006 |
| WO | WO2006031879 A1 | 3/2006 |
| WO | WO2006069078 | 6/2006 |
| WO | WO2006108145 A1 | 10/2006 |
| WO | WO2007002012 A1 | 1/2007 |
| WO | WO2007002071 A1 | 1/2007 |
| WO | WO2007011341 A1 | 1/2007 |
| WO | WO2007014241 A1 | 2/2007 |
| WO | WO2007016083 A1 | 2/2007 |
| WO | WO2007016698 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen, M. e .al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology. vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blavis, Jerry, Commentary: Pubovaginal Sling Procedure, Experience with Pubovaginal Slings, pp. 93-101 (1990).

Boyles, Sarah Hamilton et al., Procedures for Urinary Incontinence in the United States, 1979-1997, Am J Obstet Gynecol, vol. 189, n. 1, pp. 70-75 (Jul. 2003).

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Capio™ CL—Transvaginal Suture Capturing Device—Transvaginal Suture Fixation to Cooper's Ligament for Sling Procedures, Boston Scientific, Microvasive®, 8 pages, (2002).

Cervigni, Mauro et al., The Use of Synthetics in the Treatment of Pelvic Organ Prolapse, Voiding Dysfunction and Female Urology, vol. 11, pp. 429-435 (2001).

Choe, Jong M. et al., Gore-Tex Patch Sling: 7 Years Later, Urology, vol. 54, pp. 641-646 (1999).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Das, Sakti et al., Laparoscopic Colpo-Suspension, The Journal of Urology, vol. 154, pp. 1119-1121 (Sep. 1995).

Debodinance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.

Decter, Ross M., Use of the Fascial Sling for Neurogenic Incontinence: Lessons Learned, The Journal of Urology, vol. 150, pp. 683-686 (Aug. 1993).

DeLancey, John, MD, Structural Support of the Urethra As It Relates to Stress Urinary Incontinence: The Hammock Hypothesis, Am J Obstet Gynecol, vol. 170 No. 6, pp. 713-1723 (Jun. 1994).

(56) References Cited

OTHER PUBLICATIONS

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).

Falconer, C. et al., Influence of Different Sling Materials of Connective Tissue Metabolism in Stress Urinary Incontinent Women, International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce With Marlex Mesh for the Treatment of Cystoceles, International Urogyhecology Journal, vol. 9, pp. 200-204 (1998).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138 (Sep. 1987).

Guner, et al., Transvaginal Sacrospinous Colpopexy for Marked Uterovaginal and Vault Prolapse, Inter J of Gynec & Obstetrics, vol. 74, pp. 165-170 (2001).

Gynecare TVT Tension-Free Support for Incontinence. The tension-free solution to female Incontinence, Gynecare VVorldwide,6 pages, (2002).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Michael et al., Predicting Treatment Choice for Patients With Pelvic Organ Prolapse, Obstetrics & Gynecology, vol. 101, n. 6, pp. 1279-1284 (Jun. 2003).

Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).

Hodgkinson, C. Paul et.al., Urinary Stress Incontinence in the Female, Department of Gynecology and Obstetrics, Henry Ford Hospital, vol. 10, No. 5, p. 493-499, (Nov. 1957).

Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).

Ingelman-Sunberg. A. et al., Surgical Treatment of Female Urinary Stress Incontinence, Contr. Gynec. Obstet., vol. 10, pp. 51-69 (1983).

Ivs Tunneller—A Universal instrument for anterior and posterior intra-vaginal tape placement. Tyco Healthcare, 4 pages (Aug. 2002).

IVS Tunneller—ein universelles Instrument fur die Intra Vaginal Schlingenplastik, Tyco Healthcare, 4 pages (2001).

Jeffcoate. T.N.A. et al., The Results of the Aldridge Sling Operation for Stress Incontinence, Journal of Obstetrics and Gynaecology, pp. 36-39 (1956).

Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).

Julian, Thomas, the Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

Karram, Mickey et al., Patch Procedure: Modified Transvaginal Fascia Lata Sling for Recurrent for Severe Stress Urinary Incontinence, vol. 75, pp. 461-463 (Mar. 1990).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Kersey, J., The Gauze Hammock Sling Operation in the Treatment of Stress Incontintence, British Journal of Obstetrics and Gynaecology, vol. 90, pp. 945-949 (Oct. 1983).

Klutke, Carl et al., The Anatomy of Stress Incontinence: Magentic Resonance Imaging of the Female Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Klutke, John M.D. et al. The promise of tension-free vaginal tape for female SUI, Contemporary Urology, 7 pages (Oct. 2000).

Korda, A. et al., Experience With Silastic Slings for Female Urinary Incontience, Aust NZ J. Obstet Gynaecol, vol. 29, pp. 150-154 (May 1989).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Kovac, Stephen Robert, M.D., Cirriculum Vitae, pp. 1-33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5. pp. 388-390 (May 1988).

Lichtenstein, Irving L. et al, The Tension Free Hernioplasty, The American Journal of Surgery, vol. 157 pp. 188-193 (Feb. 1989).

Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).

Luber, Karl M. at al., The Demographics of Pelvic Floor Disorders; Current Observations and Future Projections, Am J Obstet Gynecol, vol. 184, n. 7, pp. 1496-1503 (Jun. 2001).

Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).

Marchionni, Mauro et al., True Incidence of Vaginal Vault Prolapse—Thirteen Years of Experience, Journal of Reproductive Medicine, vol. 44, n. 8, pp. 679-684 (Aug. 199).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics. vol. 88, pp. 509-518 (1949).

McGuire, Edward J. et al., Pubovaginal Sling Procedure for Stress Incontinence, The Journal of Urology, vol. 119, pp. 82-84 (Jan. 1978).

(56) References Cited

OTHER PUBLICATIONS

McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence At the University of Michigan, Journal of Urology, vol. 138, pp. 90-93(1987).
McGuire, Edwared J. et al., Abdominal Fascial Slings, Slings, Raz Female Urology, p. 369-375 (1996).
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., a Simplified Sling Operation Suitable for Routine Use, Gynecological and Obstetrical Clinic, University of Vienna, vol. 84, No. 3, p. 400-405, (Aug. 1, 1962).
Natale, F. et al., Tension Free Cystocele Repair (TCR): Long-Term Follow-Up, International Urogynecology Journal, vol. 11, supp. 1, p. S51 (Oct. 2000).
Nichols, David H., The Mersilene Mesh Gauze-Hammock for Severe Urinary Stress Incontinence, Obstetrics and Gynecology. vol. 41, pp. 88-93 (Jan. 1973).
Nicita, Giulio, A New Operation for Genitourinary Prolapse, Journal of Urology. vol. 160, pp. 741-745 (Sep. 1998).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).
Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics. Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics. Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).

(56) References Cited

OTHER PUBLICATIONS

Petros, Peter E. Papa et al., The Intravaginal Slingplasty Operation, A Minimally Invasive Technique for Cure of Urinary Incontinence in the Female, Aust. NZ J Obstet vol. 36, n. 4, pp. 453-461 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence from Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II; Restoration of Dynamic Vaginal Supports by Infracoccygeal Sacropexy, An Axial Day-Case Vaginal Procedure, Int Urogynecol J. vol. 12, pp. 296-303 (2001).
Rackley, Raymond R. et al., Tension-Free Vaginal Tape and Percutaneous Vaginal Tape in Sling Procedures, Techniques in Urology, vol. 7, No. 2, pp. 90-100 (2001).
Rackley, Raymond R. M.D., Synthetic Slings: Five Steps for Successful Placement, Urology Times, p. 46, 48, 49 (Jun. 2000).
Raz, Shlomo, et al., the Raz Bladder Neck Suspension Results in 206 Patients, The Journal of Urology, pp. 845-846 (1992).
Raz, Shlomo, Female Urology, pp. 82-85 pp. 80-86, 369-398, 435-442 (1996).
Raz, Shlomo, Md, Modified Bladder Neck Suspension for Female Stress Incontinence, Urology, vol. XVII, No. 1, (Jan. 1981).
Richardson, David A. at al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy the "True" Prolapse of the Vaginal Stump, Clin obstet gynecol, vol. 25, pp. 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
SABRE™ Bioabsorbable Sling, Generation Now, Mentor, 4 pages (May 2002).
SABRE™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sargent. F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the of Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas a., M.D., Endoscopic Suspension of the Vesical Neck for Urinary Incontinence in Females, Ann. Surgery, vol. 192 No. 4 pp. 465-471 (Oct. 1980).
Stanton, Stuart L. Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin et al., A Comparison of Tensile Strength among Three Preparations of Irradiated and Non-Irradiated Human Fascia Lata Allografts (2 pages).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Suport™, Sub-Urethral Perineal Retro-Pubic Tensionless Sling, Matrix Medical (Pty) Ltd, (no date), 1 pg.
Swift, S.E., et al., Case-Control Study of Etiologic Factors in the Development of Sever Pelvic Organ Prolapse, Int Urogynecol J, vol. 12, pp. 187-192 (2001).
TVT Tension-free Vaginal Tape, Gynecare, Ethicon, Inc., 6 pages (1999).
Ulmsten, U. et al., a Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).
UroMed Access Instrument System for the Sub-urethral Sling Procedure Catalog No. 120235, Directions for Use, (3 pages).
Vesica@ Percutaneous Bladder Neck Stabilization Kit, A New Approach to Bladder Neck Suspenison, Microvasive@ Boston Scientific Corporation, 4 pages (1995).
Vesica@ Sling Kits, Simplifying Sling Procedures, Microvasive@ Boston Scientific Corporation, 4 pages. (1998).
Villet, R., Réponse De R. Villet àL'Article De D. Dargent et al., Gynecolgie Obstetrique Fertilite, vol. 31, p. 96 (2003).
Visco, Anthony G. et al., Vaginal Mesh Erosion After Abdominal Sacral Colpopexy, Am J Obstet Gynecol, vol. 184, n. 3, pp. 297-302 (297-302).
Walters, Mark D., Percutaneous Suburethral Slings: State of the Art, Presented conference of the American Urogynecologic Society, Chicago, 29 pages (Oct. 2001).
Waxman, Steve et al., Advanced Urologic Surgery for Urinary Incontinence, The Female Patient, pp. 93-100, vol. 21 (Mar. 1996).

(56) References Cited

OTHER PUBLICATIONS

Weber, Anne M. et al., Anterior Vaginal Prolapse: Review of Anatomy and Techniques Surgical Repair, Obstetrics and Gynecology, vol. 89, n. 2, pp. 311-318 (Feb. 1997).
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology and Nephrology, Supplement 153: p. 1 (1993).
Mentor Porges, Uratape, ICS/IUGA Symp, Jul. 2002.
Kettel, L. Michael et al., An Anatomical Evaluation of the Sacrospinous Ligament Colpopexy, Surg. Gynecol. Obstet., 168(4):318-22, Apr. 1989.
Flynn, B.J. et al., Surgical Management of the Apical Vaginal Defect, Curr. Opin. Urol. 12(4):353-58, Jul. 2002.
Buller, J.L. et al., Uterosacral Ligament: Description of Anatomic Relationships to Optimize Sergical Safety, Obstet. Gynecol. 97:873-79, 2001.
Brochure, "Gps for Pelvic Floor Repair," Gynecare Prolift, 6 pages, 2005.
Greene, Frederick, "Repair of Rectal Prolapse Using a Puborectal Sling Procedure,"Arch Surg; vol. 118, pp. 398-401 (Apr. 1983).
Shafik, Ahmed, "Puborectoplasty, New Technique for the Repair of Fecal Incontinence," Dig. Surg. 1991; 8: pp. 182-186.
Precision Twist, Low Profile design for Precise Anchor Placement, Boston Scientific Microvasive, 2001 2 pp.
Vesica Sling Kit, Microvasive Boston Scientific, 1997 6pp.
Precision Tack, The Precise Approach to Transvaginal Sling Procedures, Boston Scientific, 1998, 4pp.
Horn H, et al, Sphincter Repair with a Silastic Sling for Anal Incontenence and Rectal Procidentia. Diseases of the Colon & Rectum 28: 868-72, 1985.
Dean P. et al, Silicone Elastomer Sling for Fecal Incontinence in Dogs, Vet Surg, vol. 17, No. 6, pp. 304-310, 1988.
Yamana T, Takahashi T, Iwadare J. Perineal Puborectalis Sling Operation for Fecal Incontinence: Preliminary Report. Diseases of the Colon & Rectum 47: 1982-89, 2004.
McMahan et al., Rectal prolapse. an update on the rectal sling procedure,: Am Surg., vol. 53, No. 1, pp. 37-40, 1987.
O'Rourke D, et al., "A puborectal sling in the management of anal incontinence and rectal prolapse," Aust N Z J Surg., vol. 55, No. 5, pp. 493-495, 1985.
O'Rourke D, et al., "An anorectal sling in the treatment of rectal prolapse and incontinence," Aust N Z J Surg., vol. 44, No. 2, pp. 144-146, 1974.
Holschneider The use of a levator ani sling in anal incontinence,: An Esp Pediatr., vol. 13, No. 4, pp. 335-338, 1980.

* cited by examiner

SURGICAL IMPLANTS, TOOLS, AND METHODS FOR TREATING PELVIC CONDITIONS

PRIORITY CLAIM

This application claims benefit from International Application No. PCT/US2007/014120, having PCT Publication No. WO 2007/149348, which was filed on 15 Jun. 2007, which in turn claims priority to U.S. Provisional Patent Application having Ser. No. 60/805,040, filed on Jun. 16, 2006, titled PELVIC FLOOR REPAIR TISSUE FIXATION, U.S. Provisional Patent Application having Ser. No. 60/897,697, filed Jan. 26, 2007, titled ARM LENGTH REDUCTION/TENSIONING CONCEPT, and U.S. Provisional Patent Application having Ser. No. 60/863,055, filed Oct. 26, 2006, titled PELVIC MESH IMPLANT ADJUSTMENT DEVICE, the entire content of each application being incorporated herein by reference.

FIELD OF THE INVENTION

The invention relates to apparatus and methods for treating pelvic conditions by use of a pelvic implant to support pelvic tissue. The pelvic conditions include conditions of the female or male anatomy, and specifically include treatments of female or male urinary and fecal incontinence, and treatment of female vaginal prolapse conditions including enterocele, rectocele, cystocele, vault prolapse, and any of these conditions in combination. Particular examples of articles and tools described herein include: surgically implanted implants that support pelvic tissue and that can are adjustable in terms of their length or tension, during or after being implanted; implants having multiple layers, and implantation tools having various configurations.

BACKGROUND

Pelvic health for men and women is a medical area of increasing importance, at least in part due to an aging population. Examples of common pelvic ailments include incontinence (fecal and urinary) and pelvic tissue prolapse (e.g., female vaginal prolapse). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

One cause of urinary incontinence is damage to the urethral sphincter. Other causes include the loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence, and fistulas.

The female's natural support system for the urethra is a hammock-like supportive layer composed of endopelvic fascia, the anterior vaginal wall, and the arcus tendineus. Weakening and elongation of the pubourethral ligaments and the arcus tendineus fascia pelvis, and weakening of the endopelvic fascia and pubourethral prolapse of the anterior vaginal wall, may have a role in the loss of pelvic support for the urethra and a low non-anatomic position that leads to urinary incontinence.

In general, urinary continence is considered to be a function of urethral support and coaptation. For coaptation to successfully prevent or cure incontinence, the urethra must be supported and stabilized in its normal anatomic position. A number of surgical procedures and implantable medical devices have been developed over the years to provide urethral support and restore coaptation. Examples of such surgical instruments included Stamey needles, Raz needles, and Pereyra needles. See Stamey, Endoscopic Suspension of the Vesical Neck for Urinary Incontinence in Females, Ann. Surgery, pp. 465-471, October 1980; and Pereyra, A Simplified Surgical Procedure for the Correction of Stress Incontinence in Women, West. J. Surg., Obstetrics & Gynecology, pp. 243-246, July-August 1959.

One alternative surgical procedure is a pubovaginal sling procedure. A pubovaginal sling procedure is a surgical method involving the placement of a sling to stabilize or support the bladder neck or urethra. There are a variety of different sling procedures. Descriptions of different sling procedures are found in U.S. Pat. Nos. 5,112,344, 5,611,515, 5,842,478, 5,860,425, 5,899,909, 6,039,686, 6,042,534, and 6,110,101.

Some pubovaginal sling procedures extend a sling from the rectus fascia in the abdominal region to a position below the urethra and back again. The slings comprise a central portion that is adapted to support the urethra or a pelvic organ (i.e., a "support portion" or "tissue support portion"), and two extension portions bracketing the support portion, optionally a protective sheath or sheaths encasing at least the extension portions. Although complications associated with sling procedures are infrequent, they do occur. Complications include urethral obstruction, prolonged urinary retention, bladder perforations, damage to surrounding tissue, and sling erosion.

Other treatments involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced to the retropubic space. Peripheral or extension portions of the elongated urethral sling are affixed to bone or body tissue at or near the retropubic space. A central support portion of the elongated urethral sling extends under the urethral or bladder neck to provide a platform that compresses the urethral sphincter, limits urethral distention and pelvic drop, and thereby improves coaptation. Similar attached slings or supports have been proposed for restoring proper positioning of pelvic organs, e.g., the vagina or bladder.

Elongated "self-fixating" slings have also been introduced for implantation in the body, to treat pelvic conditions such as prolapse and incontinence conditions. Self-fixating slings do not require the extension portions to be physically attached to tissue or bone. Rather, the slings rely upon tissue ingrowth into sling pores to stabilize the sling. See, for example, commonly assigned U.S. Pat. Nos. 6,382,214, 6,641,524, 6,652,450, and 6,911,003, and publications and patents cited therein. The implantation of these implants involves the use of right and left hand sling implantation tools that create transvaginal, transobturator, supra-pubic, or retro-pubic exposures or pathways. A delivery system for coupling the sling ends to ends of elongate insertion tools, to draw sling extension portions through tissue pathways, is also included. Needles of the right and left hand insertion tools described in the above-referenced 2005/0043580 patent publication have a curvature in a single plane and correspond more generally to the Bio-Arc™ SP and SPARC™ single use sling implantation tools sold in a kit with an elongated urethral sling by American Medical Systems, Inc.

In some sling implantation kits, the needle portion has a proximal straight portion extending from the handle and a distal curved portion terminating in a needle end or tip. As described in the above-referenced '003 patent, the kit may include more than one type of implantation tool (also, "insertion tool"). The kit may include one tool suitable for an outside-in (e.g. from the skin incision toward a vaginal incision) procedure and another that may be suitable for an inside-out (e.g. from the vaginal incision toward a skin incision) procedure. Surgeons that prefer an approach dictated by the surgeon's dominant hand can select the procedure and the appropriate implantation tool. Alternately, universal implantation tools (e.g., right and left sling implantation tools each suitable for both an inside-out and an outside-in approach) may be provided.

Optionally, a detachable protective sheath may encase some portion of an extension portion of a pelvic implant. Connectors (e.g., dilating connectors) may be attached to the ends of the extension portions for connecting with and end of an insertion tool. Generally speaking, the insertion tool ends are inserted axially into the connectors and the extension portions of the implant are drawn through tissue pathways trailing the connector and needle, to draw a central support portion against the pelvic tissue (e.g., the urethra) to provide support. The connectors are drawn out through skin incisions and the implant and sheath are severed adjacent to the connectors.

Similar transobturator implantation procedures for implanting a pelvic implant to support a pelvic organ, e.g., the vagina, restored in proper anatomic position, are described in commonly assigned U.S. Patent Application Publication Nos. 2005/0043580 and 2005/0065395. Alternate implantation procedures for creating tissue pathways exiting the skin lateral to the anus and implanting an implant extending between the skin incisions to support a pelvic organ, e.g., the vagina, restored in proper anatomic position, are described in commonly assigned U.S. Patent Application Publication No. 2004/0039453 and in PCT Publication No. WO 03/096929. Various ways of attaching a sheath end and implant mesh extension to a self-fixating tip are detailed in the above-referenced '450 patent, for example. Further ways of attaching extensions of an implant to an implantation tool are described in U.S. Patent Publication 2004/0087970.

SUMMARY

The present patent application describes pelvic implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

Embodiments of implants include a tissue support portion and one or more extension portion. Some implants can include multiple pieces. One piece can be a support portion piece that includes the tissue support portion, and support piece arm extending from the tissue support portion. Another piece can be an extension portion piece that attaches to the support portion piece in an adjustable fashion, such as with an attachment that includes a frictional adjusting element to adjust a length of an extension portion. The multi-piece construction and frictional adjusting element allow for adjustment of the length of the extension portion, e.g., the length as measured from a distal end of the extension portion to the central support portion.

The frictional adjusting element can be a connector or adjustable element placed at an extension portion piece or at a support portion piece, e.g., at a tissue support portion or at a support portion piece arm. The frictional adjusting element in general can include an aperture and frictional engagements for contacting a segment of implant material, e.g., an elongate segment of implant material threaded through the aperture that may be a segment of extension portion that is either from an extension portion piece or from a support portion piece (e.g., a support portion piece arm). Embodiments of frictional adjusting elements may allow for one-way adjustment such as shortening of the length of the extension portion. Other embodiments of frictional adjusting elements may allow for two-way adjustment of a length of extension portion, and a structure or mechanism that can be switched, activated, removed, closed, or opened, to lock or secure the frictional adjusting element at a selected location to prevent movement in either direction.

Examples of two-way frictional adjusting elements can include a guard or other structure that can block contact between frictional surfaces of the connector and the segment of implant during two-way adjustment of the connector. The guard can be removed to allow the frictional surfaces of the connector to engage the segment of implant and prevent relative movement. Alternately, the frictional adjusting element can include an open configuration that allows the segment of implant to freely move in two directions through the aperture, and a closed configuration that closes frictional surfaces against the segment of implant to prevent relative movement. The user (e.g., surgeon) can manipulate the element between the opened and closed configurations.

Implants of the invention can include a tissue fastener at a distal end of an extension portion. The tissue fastener can be of various types, including, as examples, a self-fixating tip that is inserted into soft tissue and frictionally retained, other forms of soft tissue anchors, biologic adhesive, a soft tissue clamp that can generally include opposing jaws that close to grab tissue, and opposing male and female connector elements that engage to secure an end of an extension portion to tissue.

A tissue fastener can be placed at and secured within internal tissue of the pelvic region to support the implant and pelvic tissue that is supported by the implant. As an example, a tissue fastener can be placed at muscle tissue of an obturator foramen, tissue of an arcus tendineus, tissue in a region of an arcus tendineus, tissue of a sacrospinous ligament, tissue in a region of a sacrospinous ligament, tissue of a coccyx region, tissue of a region of an ischial spine, tissue of coccygeous muscle, tissue of iliococcygeous muscle, tissue of a uterosacral ligament, and tissue of levator muscle.

In alternate embodiments of implants and methods, a distal end of an extension portion could be attached to bone or could extend to an external incision.

Embodiments of tissue fasteners such as self-fixating tips can be designed to engage a distal end of an insertion tool to allow the insertion tool to place the self-fixating tip at a desired tissue location by pushing.

The implants can be implanted to treat a pelvic condition by supporting pelvic tissue. According to exemplary methods, a physician identifies tissue within the pelvic region to be supported, and a tissue path through which extension portions of a pelvic implant will be passed, for support. An insertion tool and extension portion can be introduced through a medial incision to insert an implant assembly. This procedure can be performed by use of a single (medial) incision, by securing ends of extension portions to internal tissue (soft tissue, bone, fascia, etc.), or in alternate embodiments one or more extension portions may be passed from the medial incision to an external incision. One or more extension portions of the implant can be adjustable, and include a frictional adjusting element. A method can include adjusting the length of one or more extension portion to adjust the position of the implant relative to tissue to be supported, especially the tissue support portion, or the tension that is applied to the tissue support portion by the extension portion.

Exemplary methods of using an implant that includes a frictional adjusting element can include implanting an implant by securing a distal end of an extension portion to tissue in the pelvic region. The central support portion is then placed as desired, and the length of an adjustable extension portion can be adjusted.

Implants as described herein include implants (e.g., slings) for treating male or female urinary incontinence, wherein the sling includes a tissue support portion and one or multiple extension portions (e.g., 2, 4, 6, or 8). The sling can have one or more features as described herein including an adjustability feature that allows the length of one or more extension portion to be adjusted; a multi-layer or "hybrid" tissue support portion; multi-piece construction; any one or more tissue fastener as described herein; or, may be in combination with an insertion tool as described herein.

Similarly, any of the other implants described, e.g., 2, 4, or 6-legged implants, for treating prolapse, male or female fecal incontinence, etc. can include any single feature or combination of features as described herein including an adjustability feature that allows the length of one or more extension portion to be adjusted; a multi-layer or "hybrid" tissue support portion; multi-piece construction; any one or more tissue fastener as described herein; or, may be in combination with an insertion tool as described herein.

Implants, methods, and insertion tools as described may allow pelvic floor reconstruction procedures to become less invasive and easier to use for a variety of pelvic floor surgery groups. Implants described herein can be used to treat a variety of areas of the pelvic floor: anterior repairs, posterior repairs, apical support, perineal body support (address levator hiatus openings), fecal incontinence, hysterectomy repairs with vault support by means of graft augmentation with tissue fasteners placed at several different anatomical landmarks. These landmarks may be the white line, muscle, and fascial layers, ligament structures (sacrospinous, sacrotuberous, cardinal, round, uterosacrals, perineal and rectal ligaments), etc.

In one aspect, the invention relates to a multi-piece pelvic implant that includes a tissue support portion an extension portion. The pieces include: a support portion piece comprising a tissue support portion and optional support portion piece arm, and an extension portion piece. The extension portion piece is adjustably connected to the support portion piece. The implant includes a frictional adjusting element that allows adjustment of a length of the extension portion. The frictional adjusting element includes an aperture through which a segment of extension portion extends and a surface that frictionally engages the segment of extension portion. The frictional engagement can preferentially allow movement of the segment of extension portion through the aperture in one direction and inhibits movement of the segment of extension portion in an opposing direction.

In another aspect, the invention relates to a multi-piece pelvic implant that includes a tissue support portion and an extension portion. The pieces include: a support portion piece having a tissue support portion and optional support portion piece arm, and an extension portion piece. The extension portion piece is adjustably connected to the support portion piece by a frictional adjusting element that allows adjustment of a length of the extension portion. The frictional adjusting element includes an aperture through which a segment of extension portion extends, and a surface that frictionally engages the segment of extension portion. The frictional adjusting element can exhibit two configurations, a first configuration that allows two-way movement of the segment of extension portion through the aperture, and a second configuration wherein the surface frictionally engages the segment of extension portion and prevents movement of the segment of extension portion through the aperture in at least one direction.

In another aspect the invention relates to a multi-piece pelvic implant that includes a tissue support portion and extension portion. The pieces include a support portion piece having a tissue support portion and optional support portion piece arm, and an extension portion piece. The extension portion piece is adjustably connected to the support portion piece by an elongate segment of extension portion of one of the two pieces passing through an opening of the other of the two pieces. A frictional adjusting element is located on the elongate segment of extension portion to allow adjustment of a length of the extension portion. The frictional adjusting element has an aperture through which the elongate segment of extension portion extends and a surface that frictionally engages the segment of extension portion. The frictional engagement preferentially allows movement of the segment of extension portion through the aperture in one direction and inhibits movement of the segment of extension portion in an opposing direction.

In another aspect the invention relates to a surgical implant for treating a pelvic condition. The implant includes a tissue support portion and an extension portion. The tissue support portion includes multiple layers of material including a layer of synthetic material and a layer of biologic material.

In another aspect the invention relates to a surgical implant for treating a pelvic condition. The implant includes a tissue support portion, an extension portion, and a tissue clamp at a distal end of the extension portion.

In another aspect the invention relates to a surgical implant for treating a pelvic condition. The implant includes a tissue support portion, an extension portion, and a tissue fastener at a distal end of the extension portion. The tissue fastener includes a male engaging element and a female engaging element.

In another aspect the invention relates to a combination of a surgical implant and a tool useful to install the surgical implant. The surgical implant includes a support portion, an extension portion, and a self-fixating tip at a distal end of the extension portion. The tool includes a finger cot that can be placed on a finger and an end tip that engages the self-fixating tip.

In another aspect the invention relates to a combination of a surgical implant and a tool useful to install the surgical implant. The surgical implant includes a support portion, an extension portion, and a self-fixating tip at a distal end of the extension portion. The tool includes a handle and an elongate curved shaft having a proximal end and a distal end. The proximal end is connected to the handle and the distal end is connected to an end segment, through a bend. The elongate curved shaft has a length in the range from 6 to 12 inches. The angle between tangents at the ends of the curved shaft is in the range from 120 to 150 degrees. The bend has an angle in the range from 120 to 150 degrees. The end segment has a length of about 0.25 to 1 inch. The end segment comprising an end tip that engages the self-fixating tip.

In another aspect the invention relates to a combination of a surgical implant and a tool useful to install the surgical implant. The surgical implant includes a support portion, an extension portion, and a self-fixating tip at a distal end of the extension portion. The tool includes a handle and an elongate shaft having a proximal end connected to the handle and a distal end connected to a pivoting loop portion. The loop portion includes an end tip that engages the self-fixating tip.

Another aspect of the invention relates to a surgical tool useful to implant a pelvic implant. The tool includes a handle, a cannula connected to the handle, and a shape memory wire slidingly positioned within the cannula. The shape memory wire has a natural shape that is different from a shape of the cannula.

Another aspect of the invention relates to methods of treating a pelvic condition. Methods include creating a medial incision; providing a pelvic implant as described herein, an insertion tool as described herein, or a combination of implant and tool; passing the implant through the incision; and positioning the implant into a desired supporting position relative to tissue of the pelvic region.

Another aspect of the invention relates to methods of treating a pelvic condition. Methods include providing a pelvic implant as described herein, an insertion tool as described herein, or a combination of implant and tool; placing a distal end of the adjustable extension portion at tissue of the pelvic region, and adjusting the length of the adjustable extension portion.

BRIEF DESCRIPTION OF DRAWINGS

Other features and advantages of the present invention will be seen as the following description of particular embodiments progresses in conjunction with the drawings. Drawings are schematic and not to scale.

DETAILED DESCRIPTION

Figure 1:
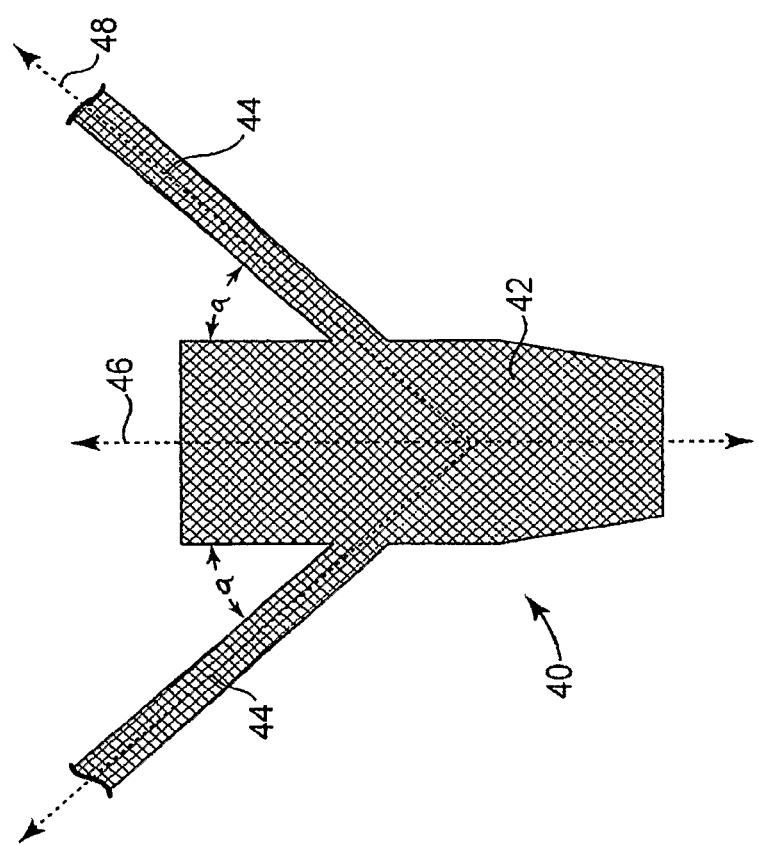
FIG. 1 illustrates a top view of a two-legged pelvic implant.

The following description is meant to be illustrative only and not limiting. Other embodiments of this invention will be apparent to those of ordinary skill in the art in view of this description.

The invention involves surgical instruments, assemblies, and implantable articles for treating pelvic floor disorders such as fecal or urinary incontinence, including stress urinary incontinence (SUI), prolapse, etc. According to various embodiments, a surgical implant can be used to treat a pelvic condition, including the specific examples of surgically placing a surgical implant to treat a condition such as vaginal vault prolapse or incontinence (male or female). Described are various features of surgical implants, surgical tools, surgical systems, surgical kits, and surgical methods useful for installing implants. An implant can be implanted in a male or a female to treat a disorder such as urge incontinence, stress urinary incontinence, mixed incontinence, overflow incontinence, functional incontinence, fecal incontinence, or a female condition including prolapse (e.g. vaginal or uterine), enteroceles (e.g. of the uterus), rectoceles, cystocele, and anatomic hypermobility, or combinations of two or more of these.

An implant can include a tissue support portion that can be used to support pelvic tissue such as the urethra (which includes the bladder neck), vaginal tissue, etc. During use, the tissue support portion is typically placed in contact with and attached to tissue to be supported, such as with a suture. An implant can additionally include one or more extension portions attached to the tissue support portion. Optionally a tissue fastener can be included at an end of an extension portion, the tissue fastener being designed to attach to tissue in the pelvic region to secure the distal end of the extension portion to the tissue.

The tissue support portion is designed to support a specific type of pelvic tissue such as the urethra, bladder, or vaginal tissue (anterior; posterior, apical, etc.). The tissue support portion can be sized and shaped to contact the desired tissue when installed, e.g., as a "sling" or "hammock," to contact and support pelvic tissue. A tissue support portion that is located between two or more extension portions is sometimes referred to herein as a "central support portion" or a "support portion."

Extension portions are elongate pieces of material that extend from the tissue support portion and are useful to pass through or attach to tissue of the pelvic region to thereby provide support for the tissue support portion and the supported tissue. One or multiple (e.g., one, two, four, or six) extension portions can extend from a tissue support portion for attachment to tissue in the pelvic region, such as by extending through a tissue path to an internal anchoring point (for attachment by bone anchor, tissue fastener, etc.), or to an external incision.

Exemplary implants can be made of materials and may be generally shaped and sized according to previous implants, but modified to include features as described herein, such as a frictional adjusting element, multi-piece construction, a multi-layer tissue support portion, etc. For example an implant can have features as described in the following exemplary documents: U.S. patent application Ser. No. 10/834, 943, filed Apr. 30, 2004; U.S. patent application Ser. No. 10/306,179, filed Nov. 27, 2002; U.S. patent application Ser. No. 11/347,063, filed Feb. 3, 2006; U.S. patent application Ser. No. 11/347,596, filed Feb. 3, 2006; U.S. patent application Ser. No. 11/347,553, filed Feb. 3, 2006; U.S. patent application Ser. No. 11/347,047, filed Feb. 3, 2006; U.S. patent application Ser. No. 11/346,750, filed Feb. 3, 2006; U.S. patent application Ser. No. 11/398,368, filed Apr. 5, 2005; U.S. patent application Ser. No. 11/243,802, filed Oct. 5, 2005; U.S. patent application Ser. No. 10/840,646, filed May 7, 2004; and International patent application number PCT/US2006/028828, having an International Filing Date of Jul. 25, 2006; the entireties of each of these disclosures being incorporated herein by reference.

Exemplary implants can be made of materials and exhibit general size and shape features that might be similar to those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

An implant may include portions or sections that are synthetic or of biological material (e.g., porcine, cadaveric, etc.). Extension portions (made of a single piece or of more than one piece) may be, e.g., a synthetic mesh such as a polypropylene mesh. The tissue support portion may be synthetic (e.g., a polypropylene mesh) or biologic.

Types of exemplary implants that can be generally useful as discussed herein can include those previously and currently used in treating pelvic conditions, including those implants referred to as urethral "slings," "strips," "mesh strips," "hammocks," among other terms for pelvic implants. Examples of implants for treating incontinence, e.g., urethral slings, can include a central support portion and two extension portions. An exemplary urethral sling can generally be in the form of an implantable strip with supportive portions consisting of or consisting essentially of a central support portion and two extension portions. Examples of urethral slings for treating male urinary incontinence can have a widened central support portion, as discussed, for example, in Assignee's copending U.S. patent application Ser. Nos. 11/347,047 and 11/347,553. Other exemplary urethral sling implants are described in Assignee's copending U.S. patent application Ser. Nos. 10/306,179; 11/347,596; 11/346,750; among others.

Examples of implants for treating vaginal prolapse can include a central support portion and from two to four to six extension portions, and may take the form of an integral piece of mesh or multiple pieces of mesh attached in a modular fashion. See, e.g., Assignee's copending U.S. patent application Ser. Nos. 11/398,369; 10/834,943; 11/243,802; 10/840, 646; PCT/2006/028828; among others.

Dimensions of an implant can be as desired and useful for any particular installation procedure, treatment, patient anatomy, and to support a specific tissue or type of tissue. Exemplary dimensions can be sufficient to allow the tissue support portion to contact tissue to be supported, and to allow extension portions to extend from the tissue support portion to a desired anatomical location to allow the extension portion to be secured to or pass through tissue of the pelvic region and support the tissue support portion.

Dimensions of extension portions according to the invention can allow the extension portion to reach between a tissue support portion placed to support pelvic tissue (at a "proximal" end of the extension portion connected to the tissue support portion) and a location at which the distal end of the extension portion attaches to pelvic tissue or passes through an external incision, as desired, according to various installation procedures.

A distal end of an extension portion, according to embodiments of the invention, can include a tissue fastener that attaches to tissue of the pelvic region. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region. The implant may also have extension portions that do not include a tissue fastener at a distal end of an extension portion, for example if the distal end is designed to be secured to tissue by other methods (e.g., suturing), or is intended to pass through an external incision.

The distal end of an extension portion can be attached to any desired tissue of the pelvic region, or passed through a desired tissue path to an external incision. To attach an extension portion to tissue, a tissue fastener can be attached at the distal end of the extension portion. During installation of the implant, the tissue fastener can be attached to any desired tissue, for example fibrous tissue such as a muscle (e.g., of the obturator foramen, obturator internus, obturator externus, levator ani, coccygeous, iliococcygeous); ligament such as the sacrospinous ligament or surrounding tissue; tendon such as the arcus tendineus or surrounding tissue; or tissue at or near the ischial spine.

As one example, an extension portion can be attached to tissue of the arcus tendineus, or to tissue of a region of the arcus tendineus, e.g., as described in Applicant's copending patent application number WO 2007/016083, published Feb. 8, 2007, and entitled "Methods and Symptoms for Treatment of Prolapse," the entirety of which is incorporated herein by reference. As described therein, an exemplary pelvic implant can be used to provide anatomical support to treat vaginal prolapse (e.g., vaginal vault prolapse, enterocele, and rectocele). The implant includes a tissue support portion attached to vaginal tissue, and one or more extension portions (e.g., exactly two extension portions) that pass from posterior vaginal tissue to a location in a region of the arcus tendineus ("white line"), optionally near the ischial spine, such as within 1 centimeter from the ischial spine. The implant can, for example, pass from the point of attachment at the vaginal tissue, through a tissue path that includes passage through tissue at the immediately anterior edge of the ischial spine and at the level of the ischial spine near the connection of the ischial spine to the arcus tendineus, and above or below the arcus tendineus.

The extension portion can extend through a tissue path that ends at the arcus tendineus, such as with a tissue fastener securing a distal end of an extension portion to the arcus tendineus. Alternately, the tissue path can wrap around the outside portion (relative to the region of the pelvic floor) of the arcus tendineus, meaning that an extension portion of an implant exits the pelvic region near the arcus tendineus (either above or below the arcus tendineus), continues along a path that wraps or bends around the white line, then (optionally) re-enters the pelvic region on the other side of the white line; i.e., below or above the arcus tendineus, whichever is opposite of the direction of entry. The tissue path can include a relatively sharp turning radius to place the extension portion near the arcus tendineus. By extending around the white line, the extension portion contacts tissue that surrounds the white line and can become ingrown into that tissue. This ingrowth can provide fixation of the extension portion into the tissue.

A preferred example of a region of the arcus tendineus can be defined as a curved-rectangular-shaped area defined to include a region that extends 2 centimeters above and 2 centimeters below (e.g., 1 centimeter above and 1 centimeter below) the arcus tendineus and that has a length starting at the ischial spine and extending in an anterior direction along the arcus tendineus, e.g., a distance of up to about 3 centimeters anterior of the ischial spine (e.g., up to about 1 centimeter anterior to the ischial spine). A particularly preferred tissue path can be very near or as close as possible to the ischial spine and either above or below the arcus tendineus, such as through tissue at the immediately anterior edge of the ischial spine and at the level of the ischial spine near the connection of the ischial spine to the arcus tendineus; dimensions can be 0.5 or 1 centimeter above or below the arcus tendineus, and 0.5 or 1 centimeter anterior to the ischial spine along the arcus tendineus.

Another example of a location for attaching an end of an extension portion is at a tissue path that passes through, or terminates at, a coccyx region as described in Applicant's copending U.S. patent application Ser. No. 11/398,368, filed Apr. 5, 2006, the entirety of which is incorporated herein by reference. That application describes the use of an implant to treat vaginal prolapse (e.g., vault prolapse, enterocele, cystocele, rectocele) using an implant that includes a tissue support portion and extension portions, wherein extension portions are passed through a tissue path that includes a region of the coccyx bone (i.e., a "coccyx region" or a "transcoccyx" tissue path).

Exemplary inventive methods involve placement of a support member to support prolapsed tissue, including placement of an extension portion of the support member at coccyx region, proximal to the coccyx bone, e.g., attached to or extending through muscle (e.g., ischiococcygeous muscle, iliococcygeous muscle), or ligament (sacrospinous ligament) lateral to the coccyx bone. Exemplary tissue paths can initiate from a region surrounding vaginal vault tissue and can extend past the rectum to a location proximal to the coccyx bone. An extension portion of the support member can generally be guided through such a passage prepared in muscle or other tissue, past the rectum, proximal to the coccyx bone, and attached to tissue internally in this region. A distal end of an extension portion can attach to any tissue of the coccyx region, such as with a tissue fastener securing a distal end of extension portion to muscle or ligament (e.g., sacrospinous ligament) in the coccyx region. Alternately, the distal end of extension portion can extend through tissue of the coccyx region and to an external incision of the epidermis.

An exemplary coccyx region can extend generally from the tip of the coccyx bone, along a side edge of the coccyx bone and continuing along a lower side edge of the sacrum to the top edge of sacrospinous ligament 202, then across to the ischial spine; a lower boundary extends between the ischial spine back to the tip of coccyx bone along a cornered path that includes a point that is approximately 2.5 centimeters lateral of the tip of the coccyx bone. An extension portion can be attached to tissue in this region, or may be passed through tissue of this region to an external incision.

Another exemplary coccyx region that can be bounded by: an edge of the coccyx bone, the lower edge of sacrospinous ligament, to the ischial spine; a point about 2.5 cm lateral to the tip of the coccyx bone, and the tip of the coccyx bone. An extension portion can be attached to tissue in this region, or may be passed through tissue of this region to an external incision.

Yet another embodiment of a coccyx region is generally the area lateral of a vertical edge of the coccyx bone, e.g., up to about 2.5 centimeters lateral of the angled vertical edge of the coccyx bone from the bottom tip of the coccyx bone to the top horizontal edge of the coccyx bone adjacent to the sacrum, e.g., a region bounded by a vertical edge of the coccyx bone between a tip of the coccyx bone at the bottom and a lower edge of a sacrum at the bottom, and a line 2.5 centimeters laterally from that edge and parallel to that edge. An extension portion can be attached to tissue in this region or may be passed through tissue of this region to an external incision.

Another example of a location for attaching an end of an extension portion is at a tissue path that passes through or terminates at a region of the ischial spine. Tissue in a region of the ischial spine can be tissue that is within one centimeter from the ischial spine, including tissue of the levator ani muscle (iliococcygeous muscle) and arcus tendineus. A distal end of an extension portion can be attached to tissue in this region, such as by a soft tissue fastener. The tissue in this region can be relatively thin compared to other tissue in the pelvic region, meaning that a tissue fastener may be adapted to securely attach to that thinner tissue. An example of a tissue fastener can be particularly useful to attach to tissue of a region of the ischial spine is a tissue clamp as described herein.

In alternate embodiments, a tissue path can pass near the ischial spine, in a region of the ischial spine, and then to other anatomy such as an external incision in a rectal or perirectal area. An example of such a tissue path is described in Applicant's copending U.S. patent application Ser. No. 10/834, 943, filed Apr. 5, 2006, the entirety of which is incorporated herein by reference. That application describes implants and methods useful for treatment of vaginal prolapse such as vault prolapse, enterocele, rectocele, the method involving a tissue path from a prolapsed organ, to a region of the ischial spine, and to an external incision. The tissue path can pass through levator muscle near the ischial spine.

Still other examples of tissue paths for an extension portion to support posterior tissue of the vagina are described in Applicant's copending U.S. patent application Ser. Nos. 11/243,802, 10/423,662, and 10/834,943, the entireties of which are incorporated herein by reference. Such tissue paths may be to the sacrum (and attached internally to the sacrum) or to an external incision in the perirectal region (e.g., through a region of the ischial spine).

Useful tissue paths and anatomy for extension portions of implants that support anterior vaginal tissue, the bladder, bladder neck, urethra, or combinations of these, can include tissue paths as described in Applicant's copending U.S. patent application Ser. Nos. 10/840,646, 10/423,662, and 10/306,179, the entireties of which are incorporated herein by reference. Such tissue paths may be to the obturator foramen, pubic bone, rectus fascia, retropubic space (attached internally), through the obturator foramen to an external incision in the thigh area, or through the rectus fascia and to an external incision in the abdomen.

As described elsewhere herein, a length of an extension portion (extended through any tissue path) can optionally be fixed or adjustable, allowing a surgeon to alter the length of an extension portion before, during, or after implantation. On the other hand, adjustment and tensioning mechanisms can also be excluded from embodiments of implants or from particular extension portions, e.g., superior extension portions that will attach to an obturator foramen, or extension portions that will be placed at a tissue path extending to an external incision.

One example of an implant for use as described herein can be a one- or two-legged implant useful to treat posterior vaginal prolapse such as vaginal vault prolapse, enterocele, rectocele, etc. Such an implant is shown at FIG. 1. Implant 40 includes central support portion 42 and one or two extension portions 44. An extension portion can optionally and preferably include an adjustability feature (not shown) that allows a length of one or two extension portions to be adjusted to adjust (lengthen or shorten) a distance between a distal end of the extension portion and a fixed position at the tissue support portion. As illustrated, extension portions 44 are at an angle (a) to longitudinal axis 46 of central support portion 42, the angle (a) being in the range from 30 to 60 degrees, e.g., from 35 and 55 degrees, or from 40 to 50 degrees, as measured from between line 46 defined by the longitudinal axis of tissue support portion 42 and a length-wise axis 48 of end portion 44, while the implant lies flat.

Still referring to FIG. 1, support portion 42 is shown to be prepared of mesh, but could alternately be of a non-mesh (e.g., biologic) material, or of multiple layers that include a non-mesh biologic layer and a synthetic mesh layer. Each extension portion 44 can optionally include a tissue fastener (not show) attached to a distal end of each extension portion 44. Such an implant can be similar to the Apogee® prolapse product sold commercially by American Medical Systems, Inc. A distal end of an extension portion, e.g., by use of a tissue fasteners, can be placed as desired, such as at internal tissue of a region of the ischial spine; muscle tissue such as coccygeous muscle, iliococcygeous muscle, or levator ani; tissue of a region of the arcus tendineus (including the arcus tendineus); tissue of a coccyx region; tissue of sacrospinous ligament; tissue the uterosacral ligament; at the sacrum (bone); etc. Alternately, the distal end may pass through any of these tissues and to an external incision.

Figure 1A:
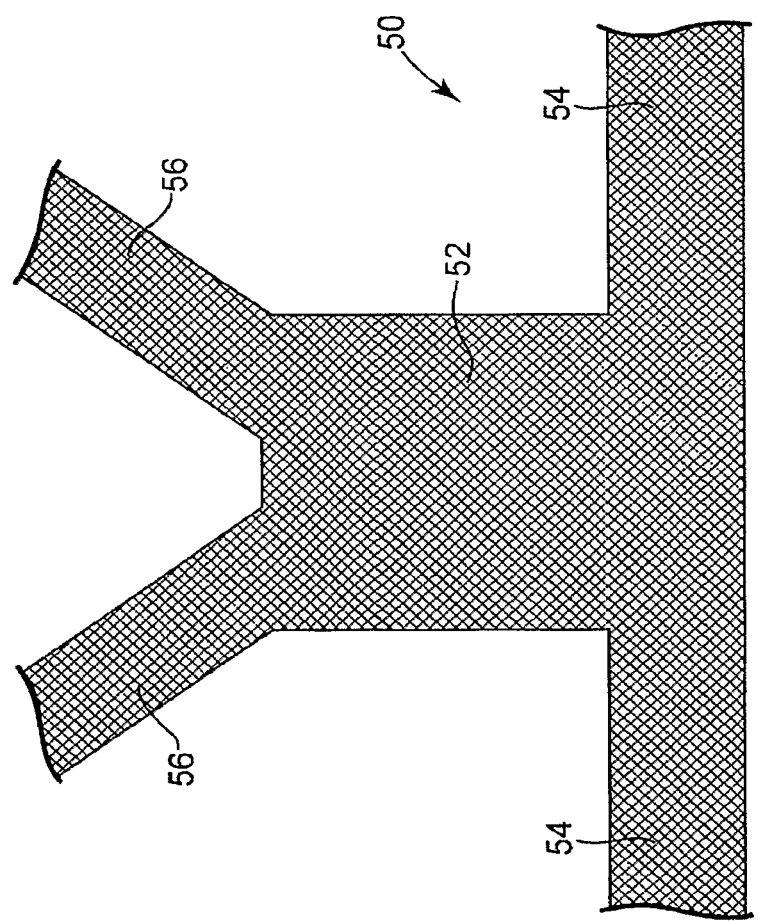
FIG. 1A illustrates a top view of a four-legged pelvic implant.

Another embodiment of implant is a four-legged implant useful to treat anterior vaginal prolapse and optionally urinary incontinence. An example of such an implant is shown at FIG. 1A. Implant 50 includes central support portion 52 and four extension portions: two superior extension portions 54 and two inferior extension portions 56. None, two, or four of extension portions 54 or 56 can include a frictional adjusting element (not shown). Superior extension portions 54 can be of fixed length or can include a frictional adjusting element.

Still referring to FIG. 1A, support portion 52 is shown to be prepared of mesh, but could alternately be of a non-mesh (e.g., biologic) material, or multiple layers that include a non-mesh biologic layer and a synthetic mesh layer. Each of extension portions 54 and 56 can optionally include a tissue fastener (not shown) attached to a distal end of each extension portion. Such an implant can be similar to the Perigee® prolapse product sold commercially by American Medical Systems, Inc. The tissue fasteners at the end of inferior extension portions 56 can be placed as desired, such as at a region of the ischial spine; at a sacrospinous ligament (e.g., within one centimeter from the ischial spine); at tissue at in a region of the arcus tendineus (including at the arcus tendineus); at tissue of the obturator foramen (e.g., obturator internus muscle); etc. Distal ends of superior extension portions 54 can be placed as desired, such as laterally toward the obturator foramen, either by attaching to the obturator foramen or passing through the obturator foramen and to an external incision; to a retropubic space; to abdominal incisions; to rectus fascia; etc.

Figure 1B:
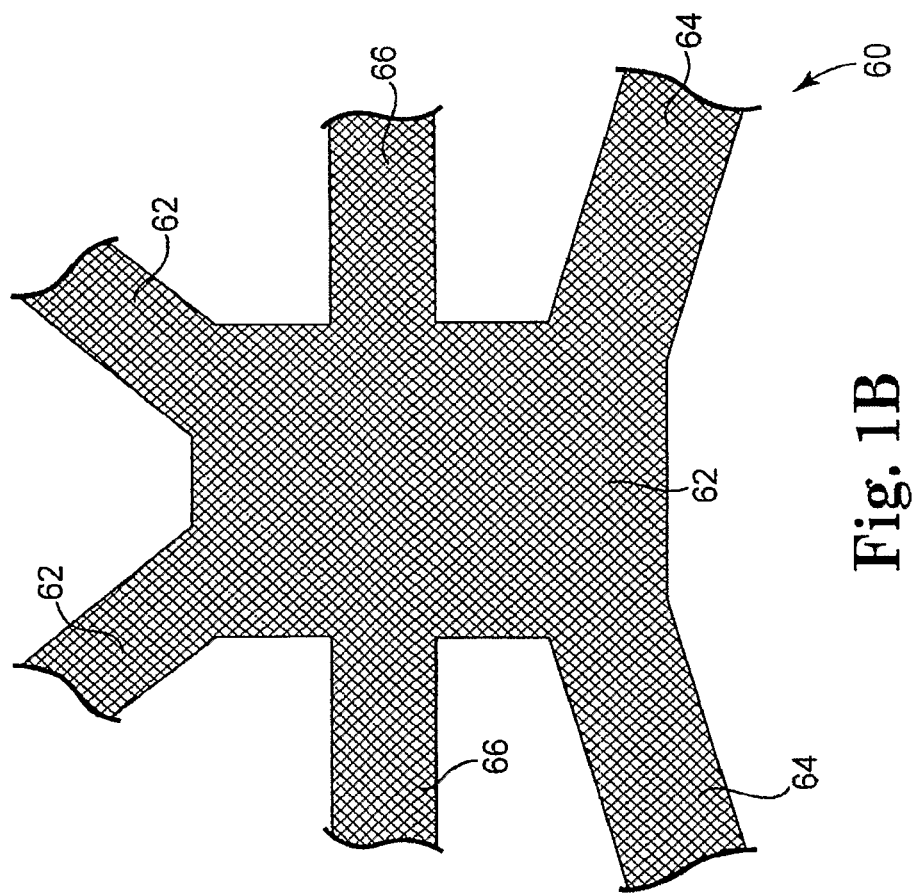
FIG. 1B illustrates a top view of a six-legged pelvic implant.

Optionally, four-legged implant 50 can include one or more additional extension portions to make, e.g., a six-legged implant, which may be useful for treating prolapse such as anterior prolapse. An exemplary six-legged implant is shown at FIG. 1B. Implant 60 includes four extension portions that can include: two superior extension portions 64 that can be, e.g., secured to the obturator foramen or alternately passed through the obturator foramen to an external incision at the inner thigh; and two inferior extension portions 62 for placement, e.g., at tissue of a coccyx region, either by internal fastening to tissue of the coccyx region (e.g., the sacrospinous ligament) or by passing through tissue of the coccyx region and to an external incision. Implant 60 includes two additional extension portions 66 that can be secured to tissue of the pelvic region as desired, such as at a region of the ischial spine, a region of the arcus tendineus, or at an obturator foramen, either by fastening to internal tissue (e.g., of the region of the ischial spine (e.g., levator ani or arcus tendineus)) or by passing through a region of ischial spine to an external incision.

Any of the implants of FIG. 1, 1A, or 1B, or any variation of these, can include one or more additional extension portions, for example for attachment to the sacrum or to the uterosacral ligament.

According to various embodiments of implants described herein, an implant can include multiple pieces that are adjustably connected together by a connecting elements that include a frictional adjusting element, to allow a length of an extension portion to be adjusted and to allow for adjustment of the position or tensioning of the implant. A "multi-piece" implant refers to an implant that includes a "support portion piece" and one or multiple "extension portion piece." The "support portion piece" is connected to the "extension portion piece" by elements that include a "frictional adjusting element," which can be used to adjust a length of an extension portion. The support portion piece includes a tissue support portion, and can optionally include one or multiple "support portion piece arms" that extend from the tissue support portion. The extension portion piece connects to the support portion piece, e.g., at the tissue support portion or at a support portion piece arm that extends from a tissue support portion of a support portion piece.

According to one general embodiment of a multi-piece implant, the support portion piece includes the tissue support portion and one or multiple "support portion piece arms" that extend from the tissue support portion to connect to the extension portion piece. A support portion piece arm can be an elongate extension of a support portion piece, generally made of a synthetic material, that connects to an extension portion piece in a manner that allows adjustment of a length of an extension portion that is made up of the support portion piece arm and the extension portion piece. The "extension portion" of the implant is considered to include the extension portion piece and the support portion piece arm, collectively. See, for example, FIGS. 2 and 2A.

According to an alternate embodiment of multi-piece implant, a support portion piece is substantially the same as the tissue support portion. The support portion piece includes a location for an elongate extension portion piece to adjustably connect to the support portion piece. See, for example, FIG. 10A.

A frictional adjusting element may be secured (i.e., fixedly and non-movably attached, as opposed to movably engaged) to an implant at a tissue support portion or at a location along the length of an extension portion (which may be part of an extension portion piece or a support portion piece arm). When secured to an extension portion, a frictional adjusting element can preferably be secured to either a distal end of a support portion piece arm, or a proximal end of an extension portion piece. A segment of the implant, e.g., an elongate piece of extension portion (which may be part of an extension portion piece or part of a support portion piece arm) may be threaded or otherwise pass through an aperture of the frictional adjusting element. The frictional adjusting element can frictionally engage the segment of implant by a frictional surface, e.g., teeth, jaws, or other opposing frictional surfaces, to allow one-way or two-way relative movement between the frictional adjusting element and the segment of implant, or to prevent relative movement in one direction or two directions.

Certain exemplary implants according to the invention can include a tissue support portion that includes multiple layers, one layer that is made of a biologic material and one layer that is made of a synthetic material such as a polymeric mesh. The multiple layers can optionally be of the same size and shape, similar sizes and shapes, or different sizes and shapes.

A multi-layer tissue support portion can include a biologic layer that is sized and shaped to contact tissue to be supported (e.g., vaginal tissue) and can have a synthetic layer that is of the same size and shape as the biologic layer, to produce a tissue support portion of two co-extensive layers. In this embodiment, a tissue support portion can include, e.g., a synthetic mesh layer and biologic layer that are identical or substantially-identical in shape and size; the mesh layer may additionally include one or more support portion piece arm or arms that extend beyond the area of the biologic layer.

Two layers of a multi-layer tissue support portion may be formed and held together as desired, such as by stitching, sutures, staples, adhesive, thermoforming, polymeric rivets, etc. In use, a biologic layer can be place adjacent to sensitive tissue such as vaginal tissue, e.g., to prevent tissue erosion.

In alternate embodiments a biologic layer can be sized and shaped to contact and support tissue, and a synthetic layer can be of a smaller area, e.g., located to extend side-to-side across a width of the tissue support portion (see e.g., FIGS. 23 and 24) to reinforce the tissue support portion at that location. The synthetic mesh layer can be in the form of a "band" or "strip" of material that extends across the width of the tissue support portion. The length of the synthetic strip can be the same as the width of the tissue support portion, or can be greater than the width of the tissue support portion, in which case the extending ends of the synthetic strip can form an extension portion or partial extension portion, e.g., a support portion piece arm that can be attached to an extension portion piece.

An example of a particular type of pelvic implant is the type that includes supportive portions including or consisting of a central support portion and two, four, or six elongate extension portions extending from the central support portion. An implant that has exactly two extension portions can be of the type useful for treating, e.g., urinary incontinence, anterior vaginal prolapse, posterior vaginal prolapse; an implant having four or six extension portions can be useful for treating combinations of these conditions. The term "supportive portions" refers to portions of an implant that function to support tissue after the implant has been implanted, and specifically includes extension portions (including frictional adjusting elements and tissue fasteners) and a tissue support portion, and does not include optional or appurtenant features of an implant such as a sheath or other type of connector for attaching the implant to an insertion tool.

An extension portion of an implant can include a tissue fastener at a distal end, such as a tissue, anchor, a self-fixating tip, a biologic adhesive, a tissue clamp, a set of opposing male and female connector elements.

A "self-fixating tip" in general can be a structure connected to a distal end of an extension portion, that can be implanted into tissue in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through tissue for implantation. The self-fixating tip may engage the insertion tool at an internal channel of the self-fixating tip, at an external location such as at the base, or at a lateral extension, as desired.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

A self-fixating tip may be of any form that can be inserted to tissue of the pelvic region, and that will thereafter be retained in the tissue. Exemplary self-fixating tips can include one or more lateral extensions that can increase the force required to remove the self-fixating tip from tissue after insertion into the tissue, i.e. the "pullout force." At the same time, the lateral extensions can be designed to exhibit a reduced or relatively low "insertion force," which is the amount of force used to insert the self-fixating tip into tissue. The self-fixating tip is designed to be essentially permanently placed upon insertion into tissue, with the single exception that if absolutely necessary to provide desired placement of the self-fixating tip or an attached implant, the self-fixating tip may be removed by a surgeon during an implantation procedure. The self-fixating tip, and all components of the self-fixating tip, can be of combined form and dimensions to result in these functional features. See, e.g., PCTUS2007/004015, filed Feb. 16, 2007, titled Surgical Articles and Methods for Treating Pelvic Conditions, the entirety of which is incorporated herein by reference.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient.

Alternate embodiments of self-fixating tips do not require and can exclude an internal channel for engaging an insertion tool. These alternate embodiments may be solid, with no internal channel, and may engage an insertion tool, if desired, by any alternate form of engagement, such as, for example, by use of an insertion tool that contacts the self-fixating tip at an external location such as by grasping the base (on a side or at the face of the proximal base end) or by contacting a lateral extension.

Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be connected to an extension portion of an implant in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006-0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form a self-fixating tip at an end of an extension portion. The self-fixating tip can be as described herein, for example, including lateral extensions and an internal channel.

An insertion tool can be used to install the implant. Various types of insertion tools are known, and these types of tools and modifications thereof can be used according to this description to install an implant. Examples of useful tools include those types of tool that generally include a thin elongate shaft (e.g., needle) that attaches to a handle; a handle attached to one end (a proximal end) of the shaft; and an optional distal end (or "end tip") of the shaft adapted to engage an end of an extension portion, e.g., a self-fixating tip. The needle can facilitate placement of the distal end of the extension portion at a desired anatomical location, that may be internal or through a tissue path to an external incision.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; and PCT application number 2006/0260618; each of which is incorporated herein by reference. Tools described in these patent documents are designed for placement of an implant in a pelvic region for the treatment of prolapse, male or female incontinence, etc. The tools may be curved in two or three dimensions, and may include, for example, a helical portion in three dimensions for placing an extension portion of an implant through a tissue path that passes from a region of the urethra, through an obturator foramen, to an external incision in the groin or inner thigh area. Other described insertion tools include a two-dimensional elongate needle that allows a user to place an extension portion of an implant through an external incision in the perirectal or coccyx region of the lower back and buttock area.

Exemplary insertion tools can be similar to or can include features of tools described in the above-referenced patent documents. For use according to certain methods described herein, those insertion tools may be modified, such as to allow the insertion tool to be used to place a self-fixating tip at tissue within the pelvic region through a tissue path that does not extend to an external incision. The insertion tool can be designed, shaped, and sized, to include an elongate shaft that may be straight or that may be curved in two or three dimensions, that can be inserted through a vaginal incision (for female anatomy) or through a perineal incision (for male anatomy), and extend from that incision to or through pelvic tissue for placement of a distal end of an extension portion.

Figure 2:
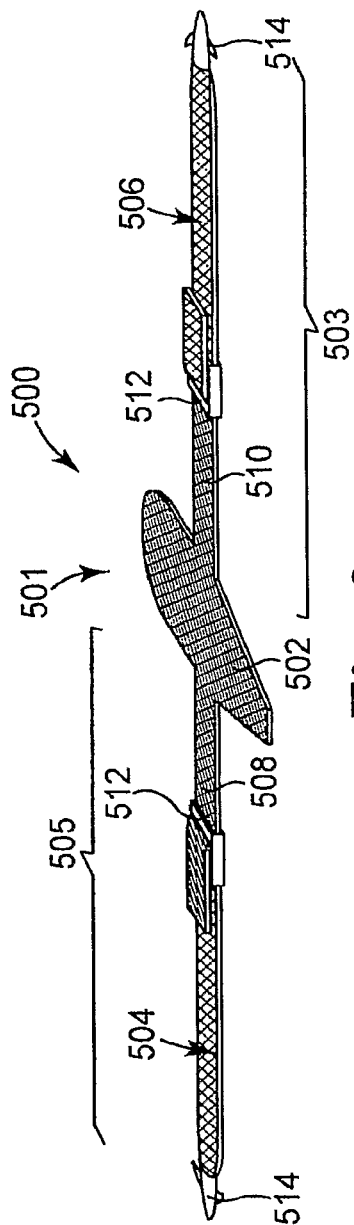
FIG. 2 illustrates a perspective view of a multi-piece implant according to the invention.
Figure 2A:
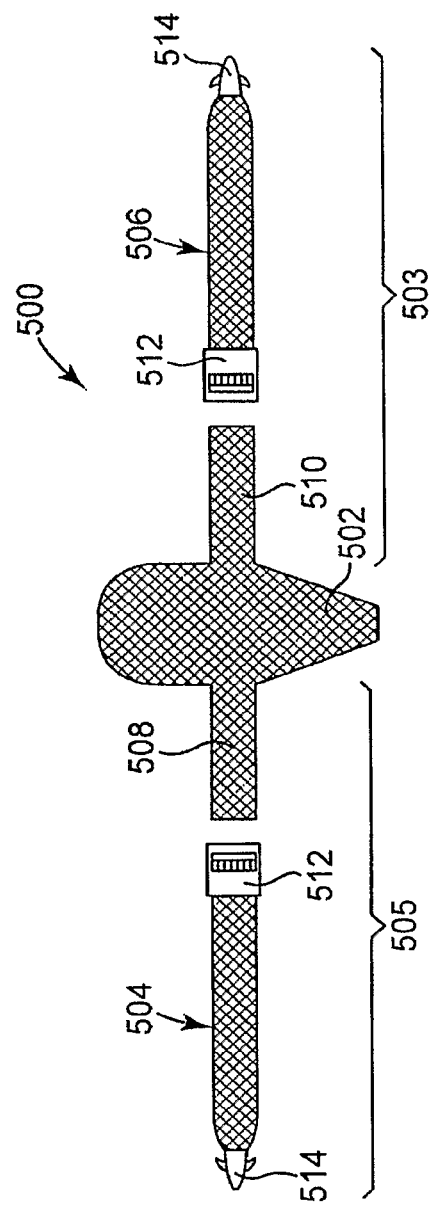
FIG. 2A illustrates a top view of the implant of FIG. 1.

FIG. 2 illustrates an exemplary multi-piece implant 500. In FIG. 2A, implant 500 is shown as an exploded view. Implant 500 includes support portion piece 501, first extension portion piece 504, and second extension portion piece 506. Support portion piece 501 includes tissue support portion 502 and first and second support portion piece arms 508 and 510. First extension portion piece 504 includes frictional adjusting element 512 secured to a proximal end, and tissue fastener (e.g., self-fixating tip) 514 at a distal end. Similarly, second extension portion piece 506 includes frictional adjusting element 512 secured to a proximal end, and tissue fastener (e.g., self-fixating tip) 514 at a distal end. Support portion piece arm 508 and extension portion piece 504 combine to produce extension portion 505. Support portion piece arm 510 and extension portion piece 506 combine to produce extension portion 503.

According to some embodiments of implants, a frictional adjusting element can be located between a support portion piece arm of an extension portion piece, and an extension portion piece, at a location to prevent the adjusting connector from contacting sensitive tissue being supported by the tissue support portion (e.g., vaginal tissue) upon installation. In certain implant embodiments a frictional adjusting element may be placed at a location that is closer to a distal end of an extension portion than to a tissue support portion of the implant; for example, a length of extension portion between a frictional adjusting element and self-fixating tip can be in the range from about 0.5 cm and about 1.0 cm.

Figure 3:
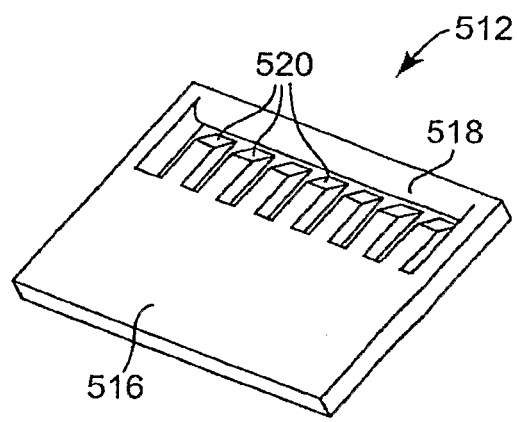
FIGS. 3 and 4 illustrate an embodiment of a frictional adjusting element according to the invention.
Figure 4:
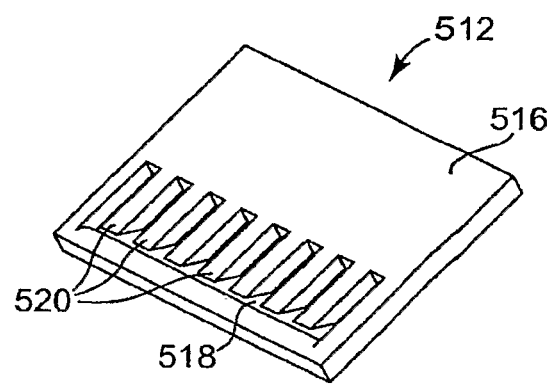
Figure 5:
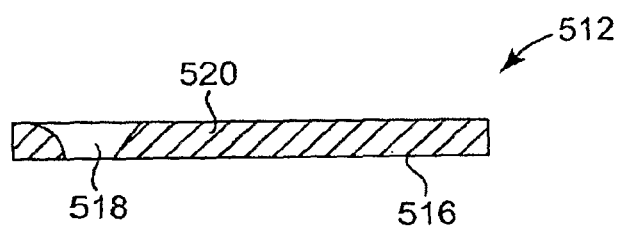
FIG. 5 illustrates a cross-sectional view of the frictional adjusting element of FIGS. 3 and 4.

Referring to FIGS. 3, 4, and 5, frictional adjusting element 512 is shown in greater detail. FIG. 3 shows a top perspective; FIG. 4 shows a bottom perspective; and FIG. 5 shows a cross-sectional view. Frictional adjusting element 512 includes body 516, aperture 518, and multiple teeth 520. Aperture 518 receives a segment of implant, e.g., support portion piece arm (508 or 510). When support portion piece arm 508 or 510 extends through aperture 518, teeth 520 frictionally grip the material of support portion piece arm 508 or 510 to provide an adjustable (one-way) connection between support portion piece 501 and an extension portion piece (504 or 506). Teeth 520 are shaped to allow support portion piece arm 508 or 510 to move through aperture 518 in an adjust direction, and prevent movement through aperture 518 in an opposite direction; ends of teeth 520 are pointed and sloped to allow movement in the adjust direction and to frictionally engage material (e.g., mesh) of the support portion piece arm to prevent movement in the opposite direction. By allowing movement in only one direction, frictional adjusting elements 512 allow one-way adjustment of lengths of extension portions (503 and 505) of implant 500.

Figure 6:
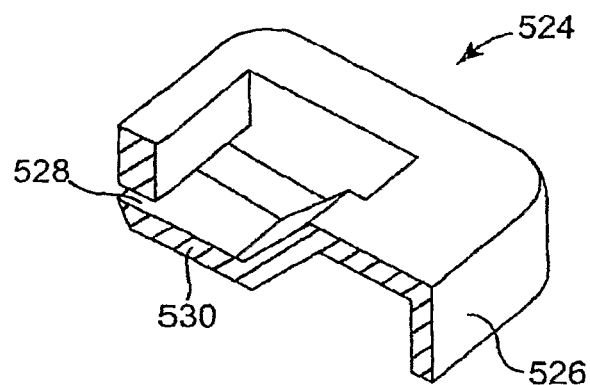
FIG. 6 illustrates a cross-sectional view of another embodiment of a frictional adjusting element according to the invention.

FIG. 6 illustrates another frictional adjusting element, 524, in accordance with the present invention, in cross-section. Frictional adjusting element 524 includes body 526, aperture 528, and multiple teeth 530. As shown, the end of tooth 530 is spaced apart from body portion 531 to define aperture 528. In use, aperture 528 can receive a segment of implant, e.g., an elongate section of support portion piece arm or extension portion piece, and teeth 530 frictionally grip the segment to provide a one-way adjustable connection between the segment of implant and the frictional adjusting element. Teeth 530 allow a segment of implant to move through frictional adjusting element 524 in an adjust direction but prevent the segment of implant from moving through the frictional adjusting element 524 in an opposite direction.

Figure 7:
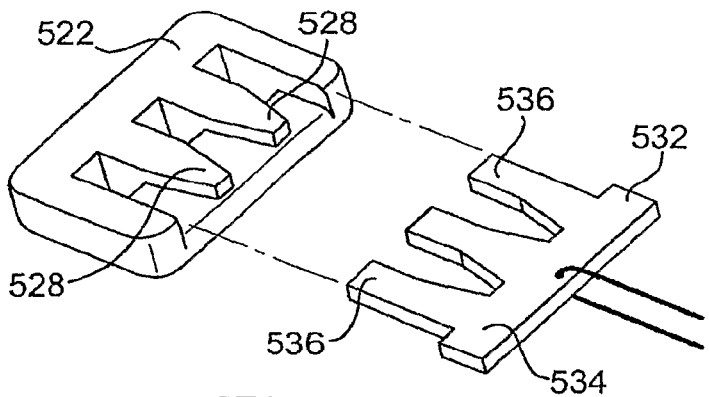
FIG. 7 illustrates an exploded view of an embodiment of a frictional adjusting element having a guard according to the invention.

FIG. 7 illustrates an embodiment of a frictional adjusting element, 522, that includes guard 532 to allow for two-way adjustment of a length of implant extension portion. Frictional adjusting element 522 includes a body, aperture, and teeth 528; a segment of implant (e.g., elongate segment of extension portion) can extend through the aperture and frictionally engage teeth 528 to prevent movement in one direction, as illustrated, or alternately in two directions. Guard 532 includes body 534 and teeth 536 that cooperatively mate with teeth 528 of frictional adjusting element 522. When guard 532 is mated with frictional adjusting element 522, a segment of extension portion (not shown) of an implant extending through the aperture of frictional adjusting element 522, in contact with teeth 528, can move through frictional adjusting element 522 in both directions and provide two-way adjustability. This is because teeth 528 of frictional adjusting element 522 are covered by guard 532, preventing teeth 528 of frictional adjusting element 522 from engaging the segment of extension portion. When guard 532 is removed or decoupled from frictional adjusting element 522, teeth 528 engage the segment of extension portion and prevent movement (in at least one direction) of the segment of extension portion, relative to frictional adjusting element 522. Preferably, as shown, a suture (as shown in FIG. 7) or the like is attached to guard 532 to facilitate removal of guard 532 from frictional adjusting element 522 at a desired time.

Figure 8:
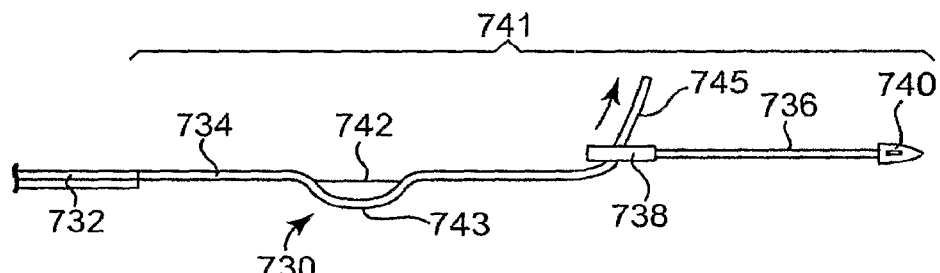
FIG. 8 illustrates an embodiment of an adjustable pelvic implant according to the invention.

FIG. 8 illustrates an exemplary adjustable pelvic implant 730. Implant 730 includes support portion piece 732 that includes support portion piece arm 734. Extension portion piece 736 is adjustably connected to support portion piece arm 734 by frictional adjusting element 738. The length of extension portion 741, comprised of support portion piece arm 734 and extension portion piece 736, can be adjusted in one direction (shortened) by pulling end 745 through frictional adjusting element 738 in the direction of the arrow. Support portion piece arm 734 cannot move through frictional adjusting element 738 in an opposite direction. Tissue fastener (e.g., self-fixating tip) 740 is at a distal end of extension portion piece 736.

As shown, support portion piece arm 734 includes suture 742 that defines a region of releasable slack 743 in support portion piece arm 734. In use, frictional adjusting element 738 provides a tensioning function while suture 742 provides a loosening function that can add length to extension portion 741; extension portion 741 can be shortened by pulling end 745 through one-way adjustable frictional adjusting element 738, and extension portion 741 can be lengthened if necessary by cutting suture 742 to release slack 743. Implant 730 thus includes a one-way adjustability feature for reducing the length of extension portion 741, and another feature to lengthen extension portion 741, if necessary or desired after use of the one-way adjustability feature.

In use, embodiments of implants of FIGS. 1-8 (and other implants having an extension portion of adjustable length) can be implanted according to methods that include placement of a tissue support portion of an implant at a location to support pelvic tissue (e.g., any pelvic tissue described herein). One or more extension portions are then placed anatomically to support the tissue support portion. For example, tissue fasteners at distal ends of extension portions can be placed at internal tissue of the pelvic region such as muscle, ligament, tendon, fascia, bone, etc., or through tissue of the pelvic region to an external incision. The length of an adjustable extension portion can be adjusted to adjust the position of the tissue support portion or to adjust the tension applied to the adjustable extension portion in supporting the tissue support portion.

Implantation can be accomplished through a medial incision such as transvaginally (for female anatomy) or perineally (for male anatomy), and by use of an insertion tool (e.g., any insertion tool described herein) that engages a distal end of the extension portion, such as by engaging a tissue fastener. Upon placement of the distal ends of extension portions, and the tissue support portion, the length of the extension portion may be reduced or lengthened by moving a segment of extension portion relative to a frictional adjusting element, to adjust the position of the support portion or the tension applied to the support portion.

According to the frictional adjusting elements of FIGS. 1 and 2, a frictional adjusting element can be secured to a proximal end of an extension portion piece, and a segment of the support portion piece arm can extend through an aperture of the frictional adjusting element. Adjustment can be performed by adjusting the amount (in terms of length) of the support portion piece arm that extends through the aperture of the frictional adjusting element. This, overall, will affect the length of material extending between the support portion and a distal end of an extension portion, e.g., an attached self-fixating tip. According to alternate embodiments of implants, a frictional adjusting element can be secured to a support portion piece, e.g., at a tissue support portion or a support portion piece arm, and a segment of the extension portion piece can extend through an aperture of the frictional adjusting element. Adjustment can be performed by adjusting the amount (in terms of length) of a extension portion piece that extends through the aperture of the frictional adjusting element.

Exemplary frictional adjusting element 512 provides one-way adjustability, while exemplary frictional adjusting element 522 provides two-way adjustability. When a segment of a support portion piece arm is pulled through frictional adjusting element 512 the teeth of the frictional adjusting element prevent the support portion piece arm from moving through the frictional adjusting element in an opposite direction. In contrast, frictional adjusting element 522 (with guard 532 installed) allows a segment of a support portion piece arm to move through the frictional adjusting element in both directions until guard 532 is removed; after selecting desired placement and tensioning of the implant, guard 532 can be removed to maintain the desired placement and tension.

Extension portion 741 of implant 730 shown in FIG. 8 may be capable of providing either one-way or two-way adjustability. In use, adjustment is performed with the frictional adjusting element 738. If needed, suture 742 can be cut to release slack in the support portion piece arm and readjustment can be performed with frictional adjusting element 738.

Figure 9:
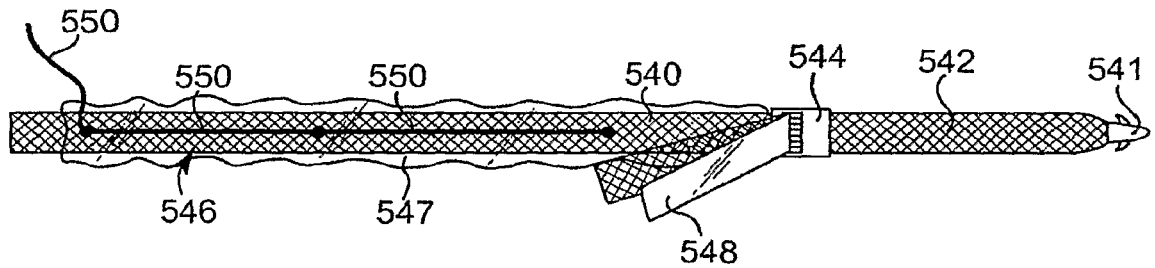
FIG. 9 illustrates a multi-piece implant or portion or multi-piece implant having a frictional adjusting element according to the invention.

FIG. 9 shows a multi-piece implant or a portion of multi-piece implant that includes frictional adjusting element 544, with sheath 546 that selectively prevents and allows engagement of teeth of frictional adjusting element 544 with the segment of implant that extends through the aperture of frictional adjusting element 544. Referring to FIG. 9, support portion piece arm 540 is shown adjustably connected to extension portion piece 542 by frictional adjusting element 544. Frictional adjusting element 544 may be a frictional adjusting elements as described herein, or any similar frictionally-engaging frictional adjusting element. Frictional adjusting element 544 can be attached to a proximal end of extension portion piece 542, and a segment of support portion piece arm 540 is received by frictional adjusting element 544. Extension portion piece 542 also includes a tissue fastener (e.g., self-fixating tip) 541 at a distal end. As shown, a film extension 548 of sheath 546 is positioned between support portion piece arm 540 and teeth of frictional adjusting element 544. Film extension 548 prevents a frictional surface (such as teeth) of frictional adjusting element 544 from frictionally engaging the mesh material of support portion piece arm 540. Support portion piece arm 540 can move through frictional adjusting element 544, in either of two directions, as long as film extension 548 of sheath 546 is this described position. When the desired position of the implant is achieved, sheath 546 and film extension 549 can be removed to allow frictional surfaces (e.g., teeth) of frictional adjusting element 544 to engage material of support portion piece arm 540 and maintain the position.

Figure 9A:
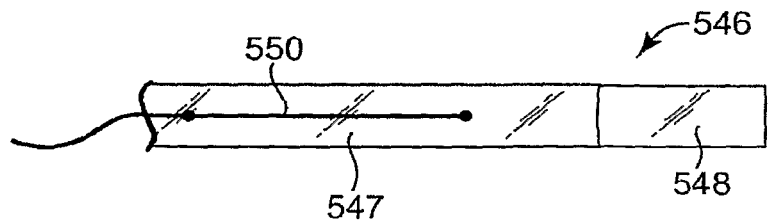
FIG. 9A illustrates a sheath of the portion of implant of FIG. 9.

Referring to FIG. 9A, sheath 546 preferably includes body 547, film extension 548, and suture 550. As shown, sheath 546 includes a proximal portion configured as a two-sided tube or envelope that can be place around and cover both surfaces of a support portion piece arm of a support portion piece. From a distal end of the tube or envelope extends a single sheet of film (extension 548) that can be inserted to pass through an aperture of frictional adjusting element 544, along with a segment of implant. Extension 548 can be placed between a frictional surface of frictional adjusting element 544, and material of a segment of implant (e.g., support portion piece arm); this configuration allows for the segment of implant to move in two directions for adjustment. Extension 548 can be removed after adjustment to allow frictional contact between frictional adjusting element 544 and the segment of implant, to prevent movement. The use of one-sided extension (548) (instead of a two-sided sheath), passing through the aperture of frictional adjusting element 544, reduces the amount of material that will pass through the aperture, reducing the force needed to move support portion piece arm 540 through frictional adjusting element 544 when adjusting.

Referring to FIG. 9, sheath 546 also preferably includes suture 550 connected at points along a length of sheath 546. Suture 550 may be heat staked or bonded to sheath 546 at one or multiple locations along a length of sheath 546. Suture 550 extends a length away from sheath 546 and during use may remain in a position (e.g., external to the patient or external of the medial incision) to allow the suture to be used to facilitate location of and removal of sheath 546. Suture 550 can also be used as a guide for physician scissors to reach toward frictional adjusting element 544 and cut the excess material extending through frictional adjusting element 544.

In use, tissue fastener 541 located at a distal end of extension portion 542 is used to secure the distal end of the illustrated extension portion to internal tissue of the pelvic region. Some time after fastener 541 is placed, sheath 546 can be cut along a length to allow the sheath to be removed. Removal of sheath 546 and extension 548, exposes support portion piece arm 540 to teeth of frictional adjusting element 544. In an optional step a physician can use suture 550 to guide scissors to trim excess material of support portion piece arm 54 that extends through frictional adjusting element 544.

Figure 10:
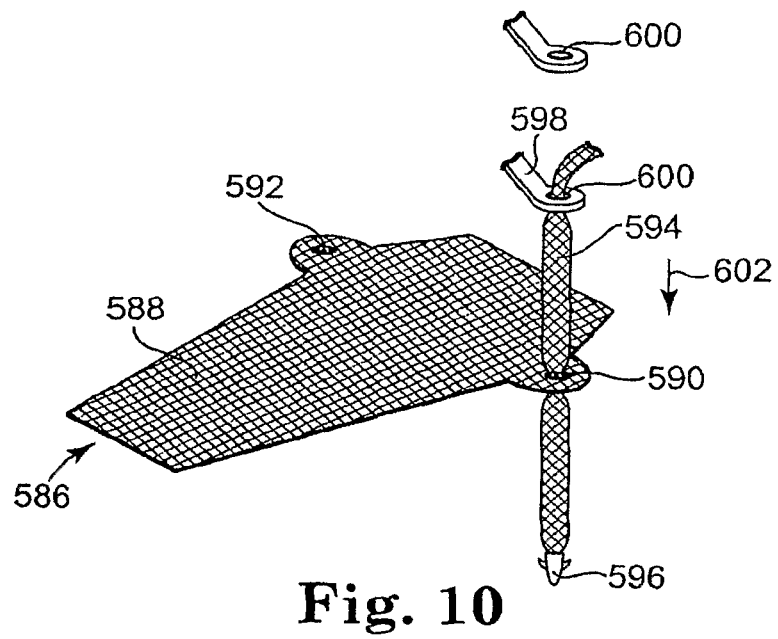
FIGS. 10 and 11 illustrate a multi-piece implant and adjustment tool according to the invention.

FIG. 10 illustrates another exemplary multi-piece pelvic implant (586). In this embodiment, one-way frictional adjusting elements are secured to a support portion piece, and a segment of an extension portion piece is adjustably engaged with the frictional adjusting element. Implant 586 includes support portion piece 588 having frictional adjusting elements 590 and 592. Frictional adjusting elements 590 and 592 include an aperture through which a segment of extension portion 594 is threaded. Multiple teeth are located to contact the segment of extension portion 594 passing through the aperture, allowing the segment of extension portion piece to move through frictional adjusting element 590 in one direction, and resist movement in the opposite direction.

Extension portion piece 594 is shown adjustably connected to frictional adjusting element 590. A segment of extension portion piece 594 extends through frictional adjusting element 590, and tissue fastener (e.g., self-fixating tip) 596 is located at a distal end of extension portion 594. Frictional adjusting elements 590 and 592 allow extension portion piece 594 to move through the frictional adjusting elements in one direction while resisting movement in the opposite direction, for adjusting the length extension portions of implant 586, as illustrated, by adjusting the amount of extension portion piece 594 that extends through frictional adjusting element 590 or 592.

Figure 11:
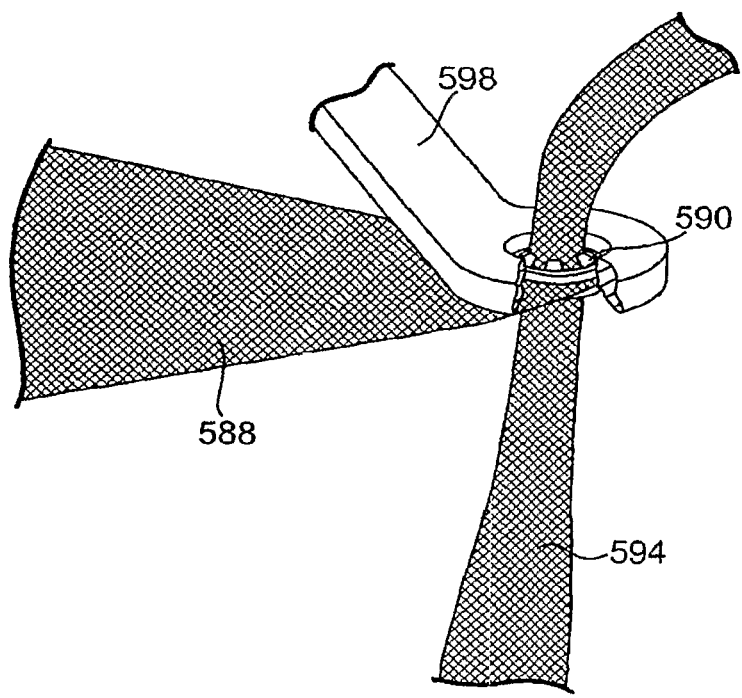

An implant such as illustrated in FIGS. 10 and 11 can be implanted, then adjusted with the assistance of an adjustment tool that helps to move one or more portions of the implant relative to each other. An exemplary adjustment tool 598 is illustrated in FIGS. 10 and 11. Tool 598, as shown, includes aperture 600 at a distal end of tool 598 that receives extension portion 594. In use, when self fixating tip 596 is anchored in tissue, tool 598 can be slid along extension portion piece 594 in adjust direction 602 until the distal end of tool 598 contacts the frictional adjusting element 590. Further movement of adjustment tool 598 in adjust direction 602 can then adjust the distance between the self-fixating tip 596 and support portion piece 588, for reducing the length of the extension portion of implant 586.

As illustrated in FIGS. 10 and 11, aperture 600 at distal end of tool 598 comprises a circular aperture sized to accommodate the material of extension portion piece 594 and to also engage a surface of frictional adjusting element 590. Thus, the diameter of aperture 600 is smaller than the outside diameter of frictional adjusting element 590 so that a surface at a distal end of tool 590, surrounding aperture 600, engages a surface (e.g., flange) of frictional adjusting element 590.

Figure 12:
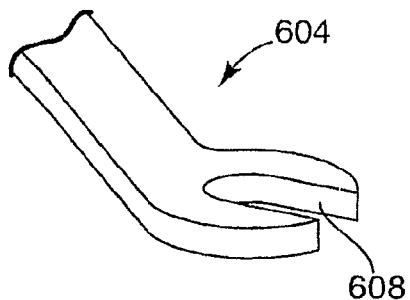
FIGS. 12 and 13 illustrate features of exemplary adjustment tools according to the invention.
Figure 13:
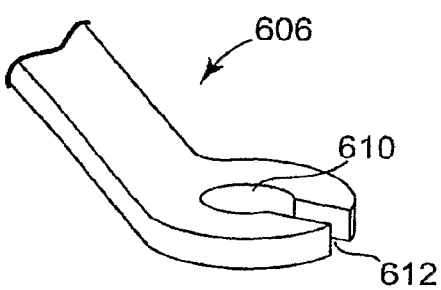

FIGS. 12 and 13 illustrate alternate embodiments of adjustment tools, 604 and 606, useful for adjusting lengths of extension portions of an implant such as implant 586. Tool 604 includes open-ended slot 608 at a distal end of tool 604, that can be slid over an extension portion (a mesh support portion piece arm, for example) and used to adjust the length of an extension portion of implant 586, e.g., a distance between tissue fastener 596 and a tissue support portion of support portion piece 588. Tool 606 includes aperture 610 and slit 612 at a distal end of tool 606. Aperture 610 is designed to function like aperture 600 of tool 598 (described above) in that aperture 610 can slide along an extension portion, and a surface at a distal end of tool 606 (or 604), surrounding aperture 610 (or 608) can engage a surface (e.g., flange) of a frictional adjusting element (not shown) to provide adjustment of a length of an extension portion. Slit 612 allows an extension portion to be fed into aperture 610 at any desired location along a length of an extension portion.

Figure 14:
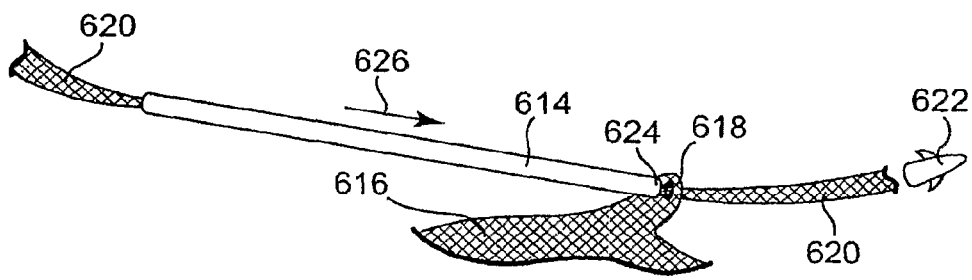
FIG. 14 illustrates a multi-piece implant and adjustment tool according to the invention.

Another embodiment of adjustment tool, tool 614, is illustrated in FIG. 14. Tissue support portion or support portion piece 616 includes (one-way) frictional adjusting element 618. Extension portion piece 620 is adjustably connected to frictional adjusting element 618. Extension portion piece 620 is connected to tissue by tissue fastener (e.g., self-fixating tip) 622 at a distal end of extension portion piece 620. Adjustment tool 614, as shown, includes a flexible or rigid tube that slides over extension portion piece 620. End 624 of tool 614 can engage a surface (e.g., flange) of frictional adjusting element 618, and tool 614 can be moved along adjust direction 626 to adjust the distance between support portion piece 616 and self-fixating tip 622.

Figure 10A:
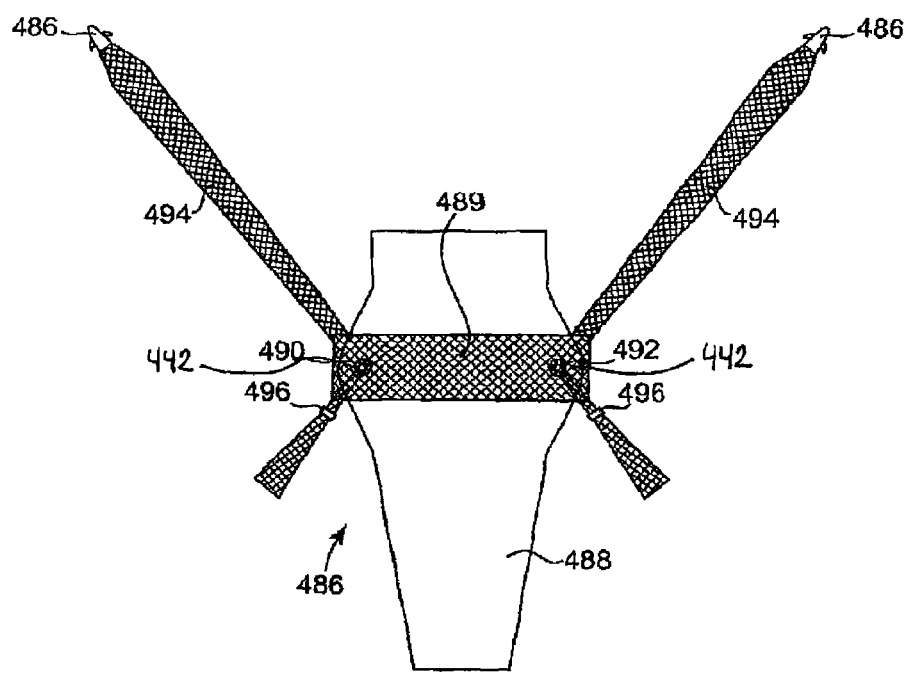
FIGS. 10A and 10B illustrate exemplary multi-piece pelvic implants according to the invention.
Figure 10B:
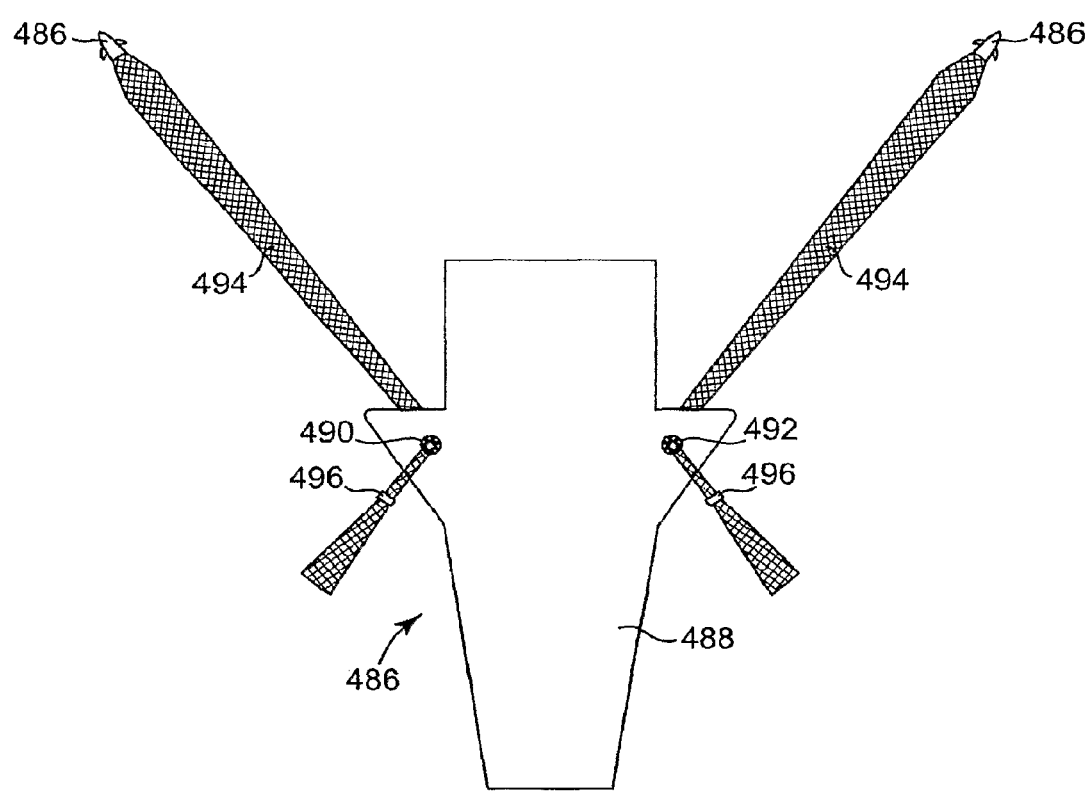

FIGS. 10A and 10B illustrate exemplary multi-piece pelvic implants (486). In these embodiments, a frictional adjusting element is moveably engaged along an extension portion piece that extends through an opening of a support portion piece; the placement of the frictional adjusting element can be moved (e.g., in an adjusting direction toward aperture 492) to adjust the length of the extension portion, e.g., as measured to be the length between the support portion piece and a distal end of the extension portion piece.

Implant 486 includes support portion piece 488 having loose apertures (e.g., grommets or openings) 490 and 492. Extension portions 494 are threaded loosely through each aperture 490 and 492 to allow two-way movement. Frictional adjusting elements 496, which may be adjustable in at least one direction and can preferably be adjustable in one direction and not the other, are located at a segment of extension portion 494 to allow frictional adjusting elements 496 to be moved along a segment of extension portion 494, closer to support portion piece 488, to allow a length between frictional adjusting element 496 and fastener 486 to be reduced (using a one-way frictional adjusting element 496) or reduced and lengthened (using a two-way frictional adjusting element 496). For example, the segment of extension portion piece 484 that is threaded through aperture 442 and then through frictional adjusting element 496 can be pulled through aperture 442 and frictional adjusting element 496, in one direction, and resist movement in the opposite direction.

In use, support portion piece 488 can be placed and adjusted into a desired position to support tissue. Self-fixating tips 486 can be placed at desired locations. To maintain the desired position of support portion piece 488, frictional adjusting elements 496 can be moved or slid along extension portion piece 494, e.g., toward self-fixating tip 486. This may be done by use of an adjustment tool as described herein. Movement of extension portion piece 494 can adjust and fix the length of extension portion piece 494 between aperture 442 and self-fixating tip 486, to adjust and maintain an anatomical position of support portion piece 488.

FIGS. 10A and 10B show openings 490 and 492 at a support portion piece of an implant, with a segment of elongate extension portion piece (494) passing through openings 492. In alternate embodiments the configuration can be similar except that the opening can be located differently on the support portion piece, e.g., at a distal end of an elongate support portion piece arm. In still other embodiments, a loose opening can be located at an extension portion piece (e.g., at a proximal end of an extension portion piece) and an elongate segment of extension portion that is part of the support portion piece, e.g., a support portion piece arm, can pass through the loose opening; a frictional adjusting element can be movably located at the support portion piece arm at a location distal to the opening 492; movement of the frictional adjusting element along the support portion piece arm, e.g., toward the tissue support portion, allows adjustment of the length of the extension portion of the implant by changing the amount of support portion piece aim that extends past the opening in the extension portion piece and also through the frictional adjusting element.

FIGS. 10, 10A, and 10B illustrate two-legged implants and various shapes of tissue support portions. Adjustable extension portions as shown in these figures can be used with any implant, such as an implant with 4, 6, or any other number of extension portions, and with any shape tissue support portion. Also, self-fixating tips 486 can be absent, or may be replaced with any other type of tissue fastener. Support portion piece 488 is illustrated to be biologic, but could be synthetic. Extension portion pieces 494 (and band 489) are illustrated to be synthetic mesh.

Figure 15:
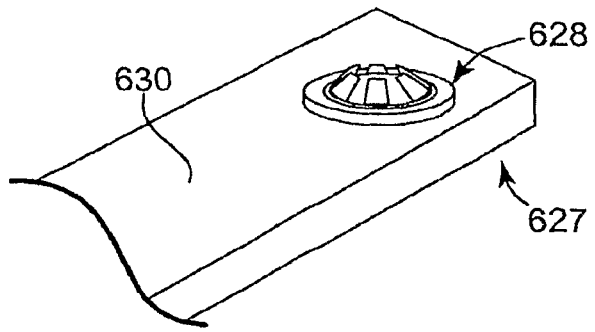
FIGS. 15-21 illustrate various embodiments of ways to attach a frictional adjusting element to an implant according to the invention.
Figure 16:
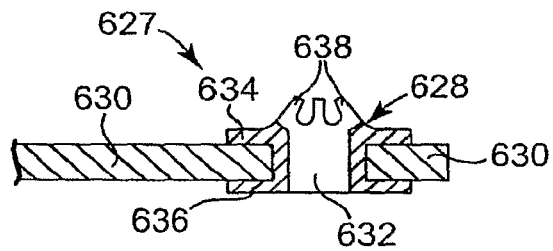

FIGS. 15-21 illustrate various embodiments of ways to secure a frictional adjusting element to an implant (e.g., to an extension portion piece, or to a support portion piece at a tissue support portion or at a support portion piece arm). FIG. 15 shows a perspective view of implant 627 having "grommet-style" frictional adjusting element 628 secured to biologic material 630. FIG. 16 is a cross-sectional view. As shown, frictional adjusting element 628 includes central aperture 632, first flange 634, second flange 636, and a plurality of flaps or "teeth" 638 extending in the direction of aperture 632. In an exemplary embodiment, the outside diameter of frictional adjusting element 628 can be about 5 mm (e.g., from 3 to 10 millimeters) and the length of a flap 638 can be in the range from about 1 mm to about 2 mm.

Figure 17:
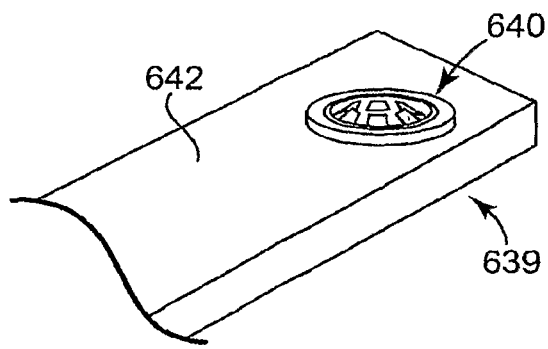
Figure 18:
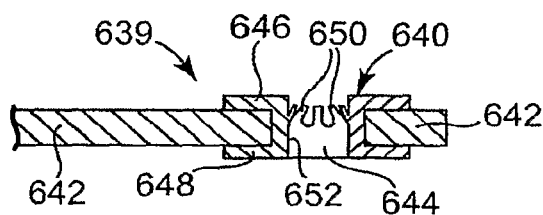

FIG. 17 shows a perspective view of another exemplary implant, 639. FIG. 18 is a cross-sectional view. Implant 639 includes frictional adjusting element 640 secured to biologic material 642, which can be a support portion piece of an implant. Frictional adjusting element 640 includes aperture 644, first flange 646, second flange 648, and a plurality of flaps or "teeth" 650 extending from inner surface 652 of aperture 644. Flaps 650 are recessed within aperture 644 and do not extend past first, flange 646. In an exemplary embodiment, the outside diameter of frictional adjusting element 640 can be about 5 mm (e.g., from 3 to 10 millimeters) and the length of a flap 650 can be in the range from about 1 mm to about 2 mm.

Figure 19:
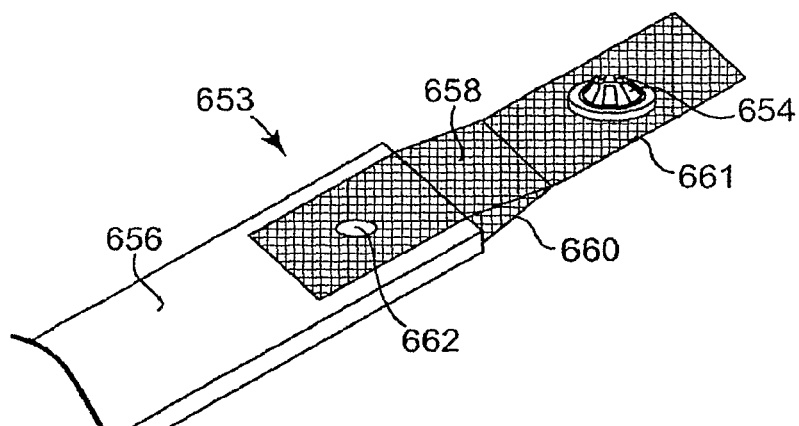
Figure 20:
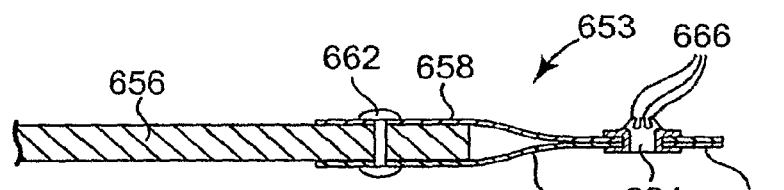

FIG. 19 shows a perspective view of implant 653, including frictional adjusting element 654, which is part of support portion piece 656 (biologic material) and support portion piece arm 661. FIG. 20 is a cross-sectional view. Implant 653 includes support portion piece arm 661 constructed of first and second portions of synthetic mesh material, 658 and 660 (connected to support portion piece 656 by rivet 662). Alternates to rivets include sutures, stitching, adhesive, thermobonding, or combinations thereof. First and second mesh portions, 658 and 660, extend past the end of biologic material 656, to form support portion piece arm 661. Frictional adjusting element 654 is located at a distal end of support portion piece arm 661. Frictional adjusting element 654 includes aperture 664 and flaps (e.g., "teeth") 666 extending toward aperture 664. Frictional adjusting element 654 is similar to frictional adjusting element 628 shown in FIGS. 15 and 16. Any frictional adjusting element as described herein can be used, such as frictional adjusting element 640 shown in FIGS. 17 and 18.

Figure 21:
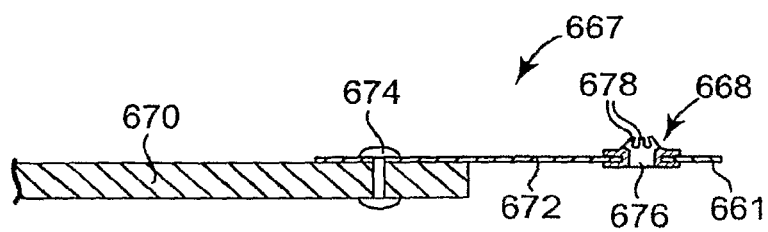

FIG. 21 shows a cross-sectional view of another implant 667 including frictional adjusting element 668 and biologic material 670. Implant 667 includes synthetic mesh support portion piece arm 672 connected to support portion piece 670 (of biologic material) by rivet 674. Mesh support portion piece arm 672 extends past the end of biologic support portion piece 670, and frictional adjusting element 668 is located toward a distal end of mesh support portion piece arm 672. As shown, frictional adjusting element 668 includes central aperture 676 and "flaps" or "teeth" 678 that extend toward aperture 676. As shown, frictional adjusting element 668 is similar to frictional adjusting element 628 shown in FIGS. 15 and 16. Any frictional adjusting element as described herein could be used, such as frictional adjusting element 640 shown in FIGS. 17 and 18.

Figure 22:
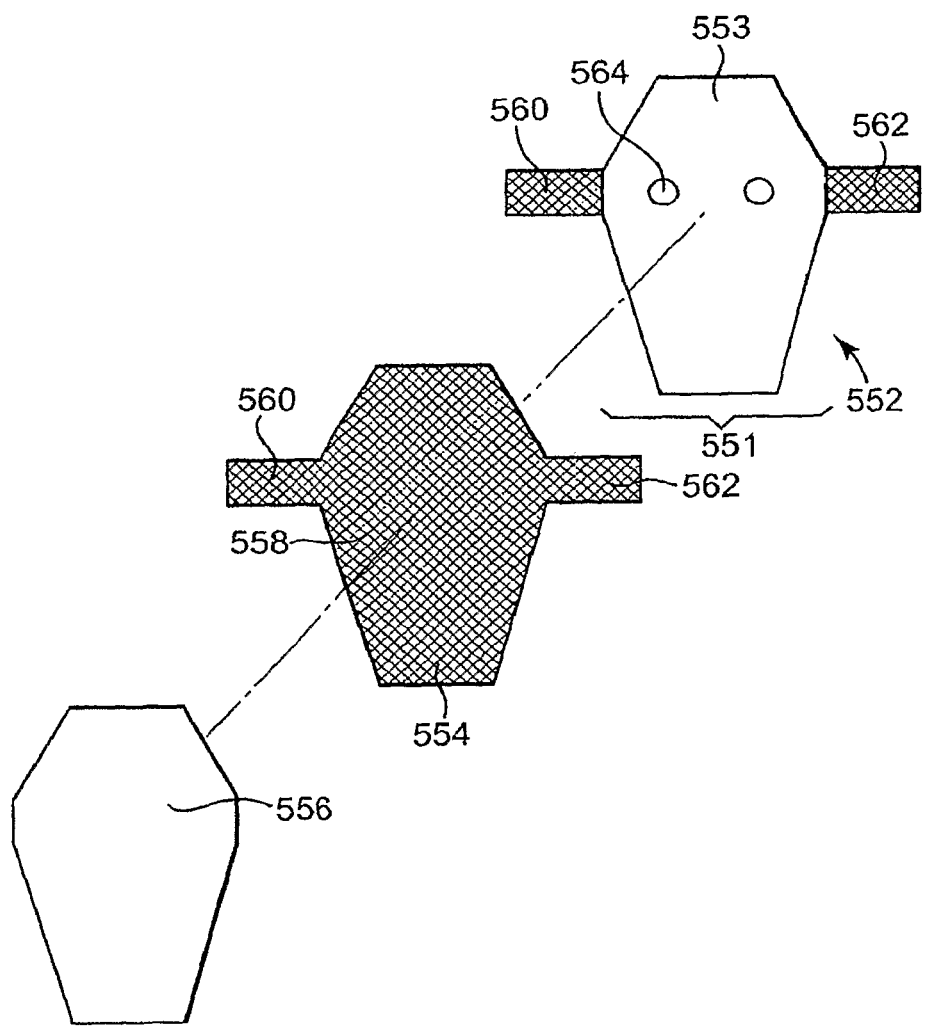
FIGS. 22-24 illustrate embodiments of multi-layer or hybrid pelvic implants according to the invention.
Figure 23:
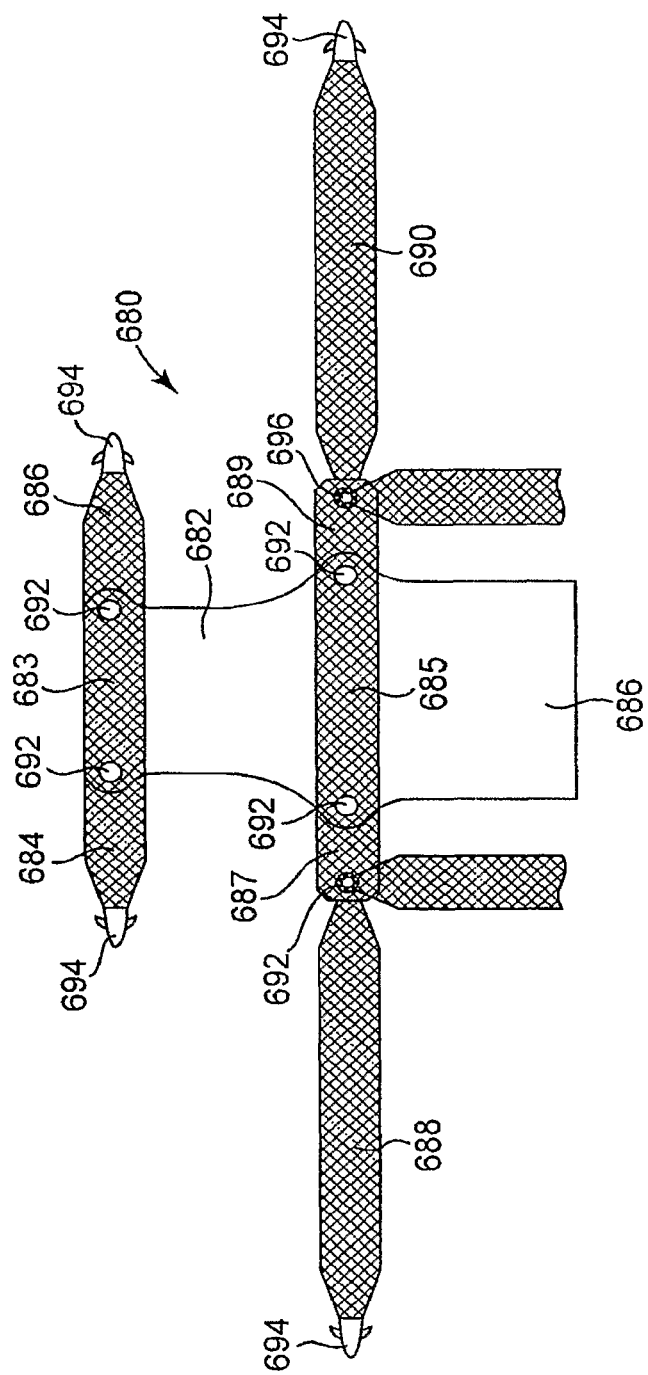
Figure 24:
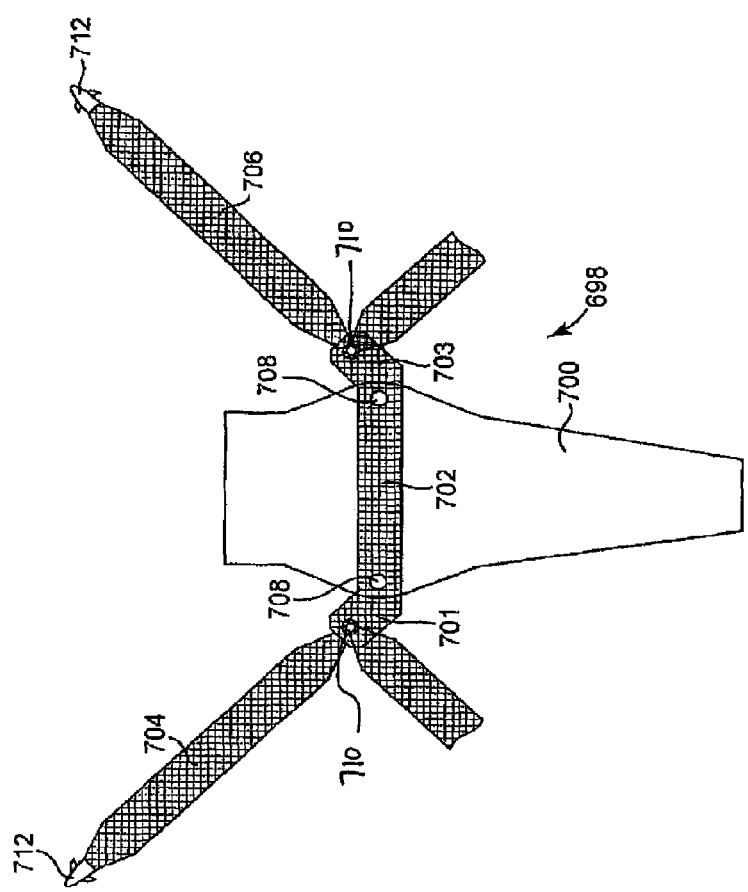

FIGS. 22-24 illustrate various embodiments of pelvic implants that include a "multi-layer" or "hybrid" tissue support portion (or support portion piece) made of two layers, one layer being a synthetic layer and a second being biologic layer. Optionally, the hybrid tissue support portion may be incorporated into any implant as described herein, such as into a support portion section of a multi-piece implant that also includes extension portions and a frictional adjusting element as described.

In FIG. 22 a portion of an exemplary pelvic implant 552 is shown in an exploded view. Implant 552 includes support portion piece 553 that includes tissue support portion 551 and support portion piece arms 560 and 562. Tissue support portion 551 includes synthetic layer 554 made of a synthetic material such as mesh, and biologic layer 556 made of a biologic material such as porcine, cadaveric, etc. Mesh layer 554 includes mesh tissue support portion 558, and first and second support portion piece arms, 560 and 562. Support portion piece arms 560 can be connected (e.g., adjustably) to extension portion pieces (not shown) of a multi-piece implant to form a multi-piece implant 552. As illustrated, biologic layer 556 generally has the same size and shape as the mesh layer 554, other than not including support portion arms 560 and 562. Support portion piece arms 560 and 562 do not include a biologic material and are of a single layer of synthetic material. Biologic layer 556 can be attached to mesh layer 554 by any useful fastener, such as by polymeric rivets 564 as illustrated, or alternately using sutures, staples, heat bonding, adhesive, etc. In use, biologic layer 556 can be positioned to contact sensitive tissue such as vaginal tissue.

FIG. 23 illustrates another exemplary hybrid or multi-layer implant. Implant 680, may be useful, for example, for treating anterior vaginal prolapse such as cystocele, optionally in combination with symptoms of urinary incontinence. Implant 680 includes support portion piece 682, that includes a tissue support portion 686 made of biologic material, and first and second mesh bands 683 and 685 attached to support portion piece 682 with rivets 692. Superior or "anterior" mesh band 683, as attached to support portion piece 682, provides first and second non-adjustable superior mesh extension portions 684 and 686, each, as illustrated, having a tissue fastener (e.g., self-fixating tip) 694 at a distal end thereof. Superior extension portions 684 and 686 may be designed to support the anterior portion of implant 680, which can support one or more of vaginal tissue, the bladder neck, or urethra, to treat vaginal prolapse and optionally to relieve symptoms of incontinence. Each tissue fastener 694 can be implanted at tissue of the obturator foramen. Alternately, superior extension portions 684 and 686 can be longer and may reach to a retropubic space, an abdominal incision, the pubic bone, or through an obturator foramen and to an external incision at the inner thigh. Superior extension portions 684 and 686 are shown to be of a fixed length, but could alternately be adjustable as described herein.

Second mesh band 685, as attached to the support portion piece 682, provides first and second support portion piece arms 687 and 689, each having a frictional adjusting element 696 secured to a distal end. First and second inferior extension portion pieces 688 and 690, having tissue fasteners (e.g., self-fixating tips) 694 at distal ends thereof, are adjustably connected to frictional adjusting element 696, as illustrated.

FIG. 24 illustrates another exemplary pelvic implant, this one being useful for treating posterior vaginal prolapse, e.g., apical or vault prolapse, enterocele, rectocele, etc. Implant 698 includes support portion piece 700 made of biologic material, and substantially making up a tissue support portion. Reinforcing mesh band 702, also a component of the support portion piece, extends across the width of support portion piece 700. Reinforcing mesh band 702 is attached to support portion piece 700 with polymeric rivets 708, and provides first and second support portion piece arms 701 and 703. First and second extension portion pieces 704 and 706 connect to support portion piece arms 701 and 703 through frictional adjusting elements 710 at distal ends of support portion piece arms 701 and 703. Extension portion pieces 704 and 706 also include tissue fasteners (e.g., self-fixating tips) 712 at distal ends thereof.

Regarding implants 680 and 698, synthetic material that may be found to be useful to make support portion pieces, support portion piece arms, extension portion pieces, and tissue fasteners, may include a variety of different plastics or other materials that are strong, while also conducive to being used in the body (e.g., biocompatible). Exemplary materials can include plastics and thermoplastics such as polypropylene, polyethylene, cellulose, polyvinyl, silicone, polytetrafluoroethylene, polygalactin, Silastic, carbon-fiber, polyethylene, nylon, polyester (e.g. dacron) PLLA, acetols, EPTFE and PGA. A synthetic implant material of a support portion piece, or extension portion piece, or tissue fastener, can independently be any of resorbable, absorbable or non-absorbable. Optionally, certain implant components may be absorbable and other portions may be non-absorbable.

In alternate embodiments the material used to make a tissue support portion may include a non-synthetic material or a combination of synthetic and non-synthetic materials.

Some example of commercially available synthetic materials include MarleX™ (polypropylene) available from Bard of Covington, R.I., Prolene™ (polypropylene) and Mersilene (polyethylene terephthalate) Hernia Mesh available from Ethicon, of New Jersey, Gore-TeX™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon.

Figure 25:
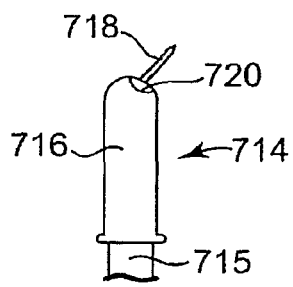
FIGS. 25-26, and 28 illustrate insertion tools for placement of an implant according to the invention.
Figure 26:
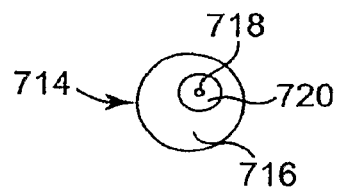

The invention also relates to insertion tools that can be useful for placement of implants. FIGS. 25 and 26 illustrate insertion driver 714 positioned on finger 715 of a user (e.g., surgeon). Insertion tool 714 includes rigid, semi-rigid, or flexible sheath 716, such as a finger cover, sheath, or finger "cot," having end tip 718 attached to a distal end of sheath 716 at a reinforced portion 720 of the sheath 716. An exemplary finger cot may be of a flexible elastomeric material such as a natural or synthetic rubber, e.g., a flexible material such as butadiene.

Figure 27:
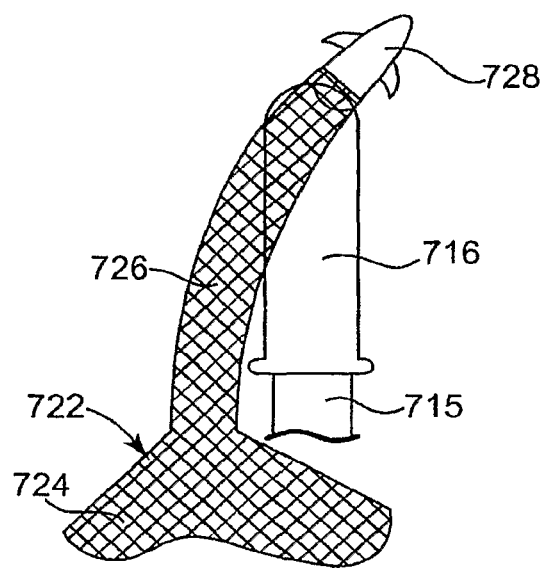
FIG. 27 illustrates the insertion tool of FIGS. 25-26 in use with a pelvic implant.

Referring to FIG. 27, insertion tool 714 is shown in use with pelvic implant 722. Implant 722 includes tissue support portion 724, extension portion 726 extending from tissue support portion 724, and self-fixating tip 728 at a distal end of extension portion 726 (extension portion 726 as illustrated is of a fixed length and does not include a frictional adjusting element, but alternately could include a frictional adjusting element). Self-fixating tip 728 includes a surface such as an internal channel that engages end tip 718. Finger cot 716 may be rigid, semi-rigid, or flexible, and can optionally be supplied in a rolled-up configuration that can be unrolled onto a finger of a user. The user can advance self-fixating tip 728 into tissue to secure self-fixating tip 728 at a desired location. Insertion tool 714 can then be retracted to separate self-fixating tip 728 from end tip 718 of tool 714.

Figure 28:
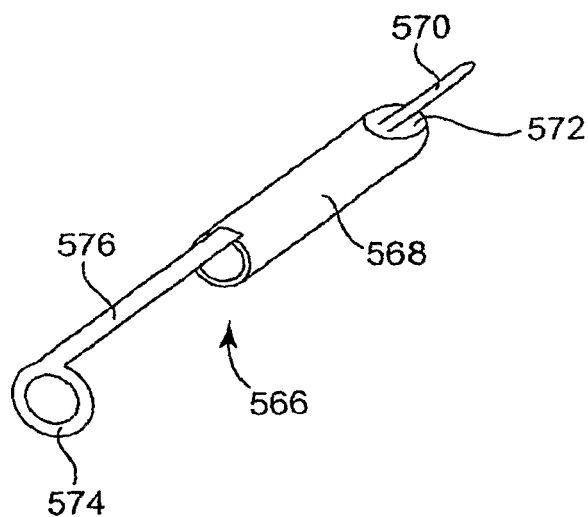

Another insertion tool, 566, is shown in FIG. 28. Insertion tool 566 is similar to insertion tool 714 and includes a flexible or non-flexible sheath 568, such as a finger cot, having an elongate tip 570 attached to sheath 568 at reinforced portion 572. Insertion tool 566 further includes finger ring 574 attached to sheath 568 through support 576. Finger ring 574 may be adjustable to accommodate different finger sizes. In use, tool 566 can be used similarly to tool 714 of FIGS. 25-27. Ring 574 and sheath 568 can be positioned on the finger of a surgeon and ring 574 and support 576 help to provide stability when implanting a self-fixating tip.

Figure 29:
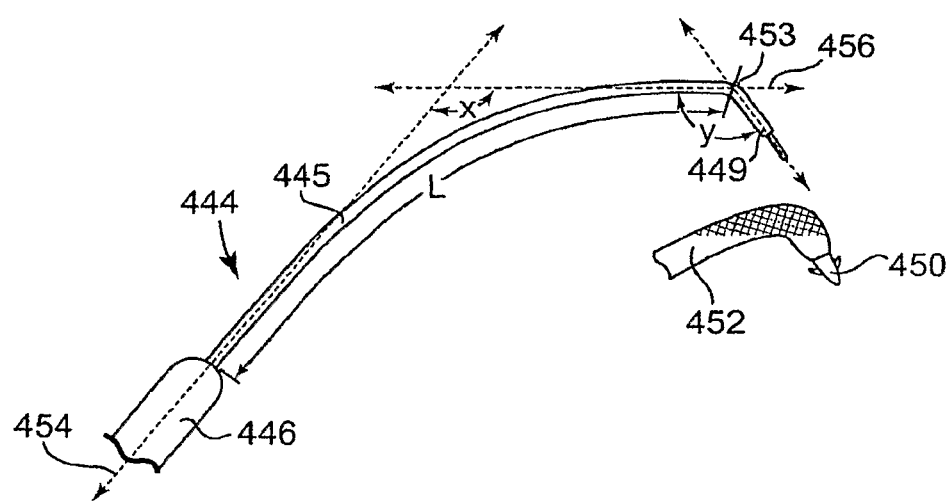
FIGS. 29, 29A, and 30-31 illustrate embodiments of insertions tools for placement of an implant.

FIG. 29 shows insertion tool 444 for inserting a self-fixating tip at a deep pelvic location such as in a region of the ischial spine, at a region of the coccyx, at a sacrospinous ligament, at a region of an arcus tendineus, etc. Insertion tool 444 includes handle 446 attached to curved shaft 445. Curved shaft 445 extends to a bend 453, after which is end tip 449 for receiving self-fixating tip 450 attached to extension portion 452. Optionally a friction fit between end tip 449 and self-fixating tip 450 can maintain the position of end tip 448 and self-fixating tip 450.

As illustrated, curved shaft 445 includes a curved segment that extends between a proximal end attached to handle 446, and a distal end that goes to bend 453. Curved shaft 445 is of length L, and can be of a combination of curves and straight sections having a total length L along the curved and straight portions. In a preferred embodiment length L (measured from handle 446 to bend 453) can be in the range from about 2 to about 10 inches (e.g., from 2 to 8 inches). The bending or curvature of shaft 445 can be as desired, e.g., gradual or in one or multiple bends, and can include straight sections and bends or curves of any of the same or different radii of curvature. End segment 449 can have a length of about 0.25 to one inch. The length of end segment 449 includes the length of end tip 448, designed to engage a self-fixating tip. The length of end tip 448 is determined by the particular self-fixating tip 450 and is chosen for a proper fit with self-fixating tip 450.

Also according to certain embodiments, angle x (defined by the intersection of tangents 454 and 456, which are tangents at the two ends of shaft 445) can be an angle in the range from 120 to 150 degrees, e.g., from 125 to 145 degrees. Angle y, which is the angle between tangent 456 and the axis of end segment 449, can be in the range from 120 to 150 degrees, e.g., from 125 to 145.

The length of end segment 449 (including end tip 448) can be selected to allow a self-fixating (e.g., tip 750) to be inserted a desired maximum depth into tissue. As illustrated (not to scale) and according to one particular embodiments, angle x can be about 132 degrees and the angle at bend 453 between tangent 449 and end segment 449 can be about 135 degrees.

A tool 444 that includes a combination of angles and lengths as specified can allow for placement (e.g., transvaginal) of a self-fixating tip at tissue deep in the pelvic region, such as tissue of a sacrospinous ligament, arcus tendineus, coccygeous muscle, iliococcygeous muscle, levator ani, ischial spine, etc., or a region near one of these tissues.

In use, self-fixating tip 450 can be positioned on end tip 449 of insertion tool 444. Insertion tool 444 is inserted through an appropriate incision (e.g., vaginal or perineal) so self-fixating tip 450 is positioned at a desired location for implantation of an end of extension portion 452. Using tool 444, force is applied to self-fixating tip 450 and the length of end segment 449 functions to limit the depth of insertion to a maximum depth. Insertion tool 444 is then removed.

Figure 29A:
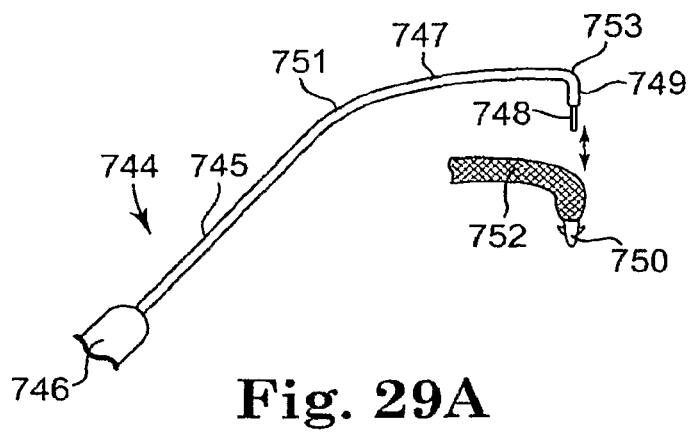

FIG. 29A shows insertion tool 744 for inserting a self-fixating tip at a deep pelvic location such as in a region of the ischial spine, at a region of the coccyx, at a sacrospinous ligament, at a region of an arcus tendineus, etc. Insertion tool 744 includes handle 746 attached to a curved or bent shaft ending at end tip 748 for receiving self-fixating tip 750 attached to extension portion 752. Optionally a friction fit between end tip 748 and self-fixating tip 750 can maintain the position of end tip 748 and self-fixating tip 750.

As illustrated at FIG. 29A, the shaft of insertion tool 744 includes three straight segments connected by two bends, including first segment 745, second segment 747, and third segment 749. In a preferred embodiment first segment 745 has a length (between handle 746 and first bend 751) in the range from about 2 to about 6 inches (e.g., from 2.5 to 5 inches), second segment 747 (from first bend 751 to second bend 753) has a length of about 2 to 4 inches (e.g., from 2.5 to 3.5 inches), and third segment 749 has a length of about 0.25 to one inch. The length of third segment 749 includes the length of end tip 748, designed to engage a self-fixating tip. The length of end tip 748 is determined by the particular self-fixating tip 750 and is chosen for a proper fit with self-fixating tip 750.

Lengths of a segment connected by a bend or curve can be measured from the center of the bend or curve. Lengths of segments 745 and 747, connected by bend 751, can be measured from the center of bend 751. Lengths of segments 747 and 749 can be measured from a center of bend 753.

According to a preferred embodiment of tool, the angle at bend 751, between first segment 745 and second segment 747, can be in the range from 120 to 150 degrees, e.g., from 125 to 145 degrees. The angle at second bend 753, between second segment 747 and third segment 749, can be in the range from 120 to 150 degrees, e.g., from 125 to 145. A radius of curvature at bend 751 can be as desired, such as in the range from 0.25 to 1.0 inches, e.g., from 0.4 to 0.8 inch. A radius of curvature at bend 753 can be as desired, such as in the range from 0.1 to 0.5 inch.

The length of third segment 749 (including end tip 748) can be selected to allow a self-fixating (e.g., tip 750) to be inserted a desired maximum depth into tissue. As illustrated (not to scale) and according to one particular embodiments, the angle at bend 751 between first segment 745 and second segment 747 can be about 132 degrees and the angle at bend 753 between second segment 745 and third segment 749 can be about 135 degrees.

A tool such as tool 744, having a combination of angles and lengths as described, can allow for transvaginal placement of a self-fixating tip at tissue deep in the pelvic region, such as tissue of the sacrospinous ligament, arcus tendineus, coccygeous muscle, iliococcygeous muscle, levator ani, ischial spine, etc.

In use, self-fixating tip 750 can be positioned on end tip 748 of insertion tool 744. Insertion tool 744 can be inserted through a medial incision (e.g., vaginal or perineal) so self-fixating tip 750 is positioned at a desired pelvic location for implantation of an end of an extension portion. Using tool 744, force is applied to self-fixating tip 750 and the length of third segment 749 functions to limit the depth of insertion to a maximum depth. Insertion tool 744 is then removed.

Figure 30:
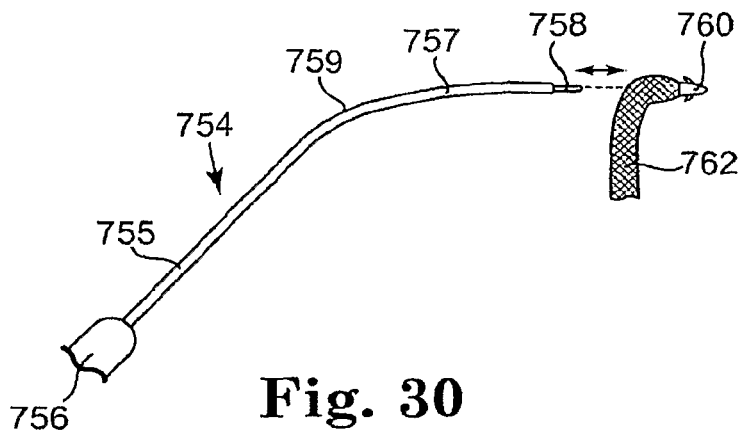

FIG. 30 illustrates another insertion tool 754 for implanting a self-fixating tip through a medial incision (e.g., a vaginal or perineal incision) at deep pelvic tissue such as at or near the sacrospinous ligament, arcus tendineus, ischial spine, or muscle of the coccygeous or iliococcygeous or levator ani. Insertion tool 754 includes handle 756 and a shaft extending from handle 756 to an end tip 758 for receiving self-fixating tip 760 attached to a distal end of pelvic implant 762. Insertion tool 754 includes first segment 755 and second segment 757. In a preferred embodiment first segment 755 can be of a length in the range from about 2 to about 8 inches (e.g., from 2.5 to 5 inches), and second segment 757 can have a length of about 2 to 8 inches (e.g., from 3 to 5 inches). The length of end tip 758 can depend on the particular self-fixating tip 760 and can be chosen for a proper fit with the self-fixating tip 760. The angle 759 between first segment 755 and second segment 757 can be in the range from 120 to 150 degrees, e.g., from 125 to 145 degrees.

In use, self-fixating tip 760 can be positioned on end tip 758 of insertion tool 754. Insertion tool 754 is inserted through a medial incision (e.g., vaginal in a female or perineal in a male) so self-fixating tip 760 can be secured at a desired pelvic tissue location. Using tool 754, force is applied to self-fixating tip 760 to the desired depth and insertion tool 744 is removed.

Figure 31:
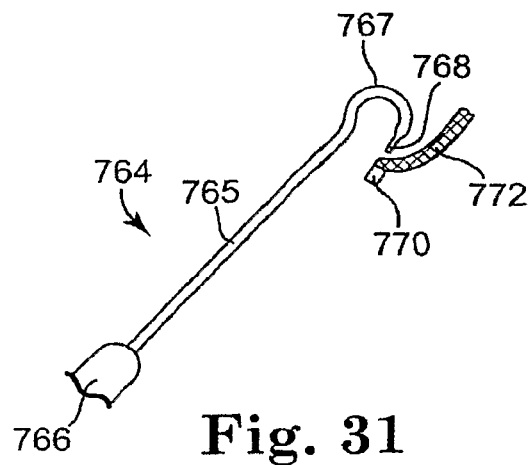
Figure 32:
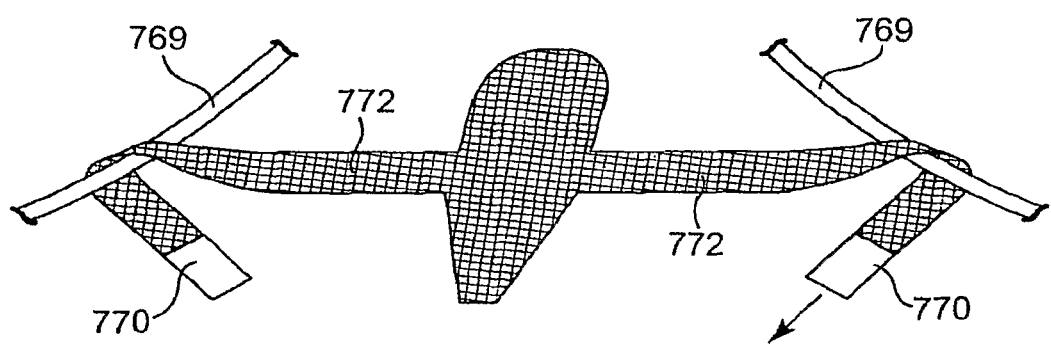
FIG. 32 illustrates an implant having extension portions positioned around the arcus tendineus.
Figure 33:
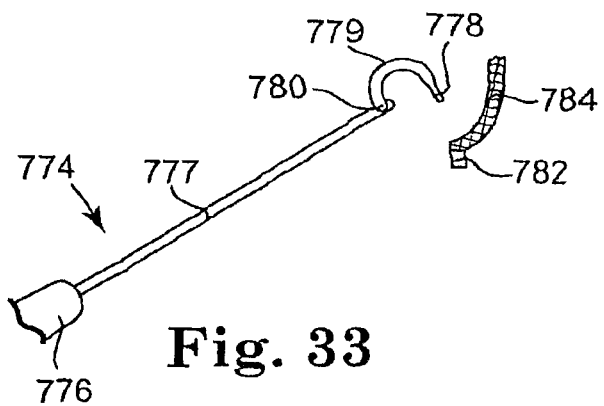
FIGS. 33-36 illustrate an insertion tool placing an implant around the arcus tendineus according to the invention.

FIG. 31 shows another embodiment of an insertion tool, tool 764, for securing a pelvic implant at the tissue deep within the pelvic region, such as at or near the arcus tendineus or at a region of the ischial spine. Insertion tool 764 includes handle 766, shaft 765, loop 767 at a distal end of shaft 765, and end tip 768 at the end of the loop 767. Loop 767 can be useful for placing a distal end of an implant at or near the arcus tendineus, such as by passing distal end of an extension portion at least partially, or fully, around the arcus tendineus. Preferably, the length of segment 765 can be in the range from about 4 to 9 inches and the diameter of loop 767 can be in the range from about 0.3 to 1.3 inch, e.g., from 0.4 to 1 inch. Insertion tool 764 can be used to position a distal end 770 of an extension portion around arcus tendineus 769 so implant 772 can be tensioned as illustrated in FIG. 32.

Figure 34:
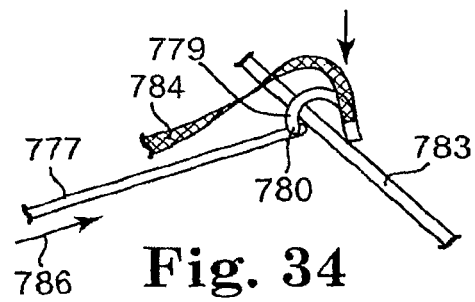
Figure 35:
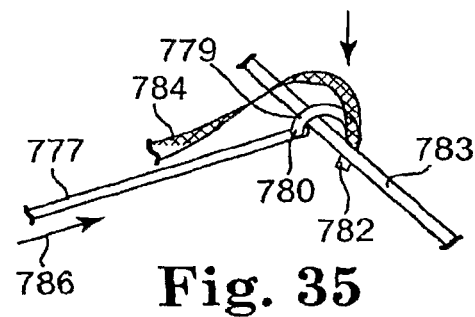
Figure 36:
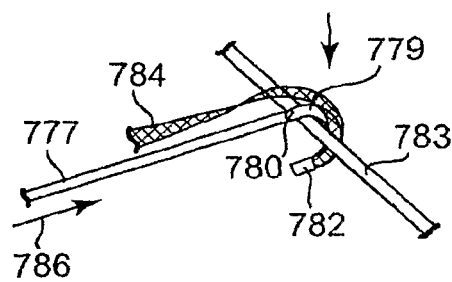

FIGS. 33 through 36 illustrate insertion tool 774 for securing a pelvic implant at tissue deep within the pelvic region, such as by placing a distal end of an extension portion at or near the arcus tendineus or in a region of the ischial spine. Insertion tool 774 includes handle 776, shaft 777, loop portion 779 that is pivotably connected to a distal end of shaft 777 at pivot point 780, and end tip 778 at the end of loop portion 779. End tip portion 778 receives a distal end 782 of implant 784. In use, as illustrated in FIGS. 34-35, insertion tool 774 is used to position distal end 782 around arcus tendineus 783. Implant 784 can then be tensioned and secured accordingly, e.g., by use of an adjustable extension portion having a frictional adjusting element.

According to preferred embodiments and methods, as insertion tool 774 is pushed along direction 786, loop portion 779 and end tip 778 pivot at pivot point 780, and distal end 782 passes around arcus tendineus 783. Preferably, loop portion 779 can be connected to shaft 777 so that desired control and movability of loop portion 779 around arcus tendineus 783 can be achieved. For example, insertion tool 774 may include additional mechanical and structural features such as springs, linkages, levers, actuators, or the like, to provide the desired functionality and control of loop portion 779 by a user by manipulation of a control mechanism located at handle 776. As one example, a mechanical linkage can connect loop portion 779 to a proximal end of the tool such as at handle 776, where a control mechanism (e.g., trigger) allows control of the position of loop portion 779 about pivot point 780.

Figure 37:
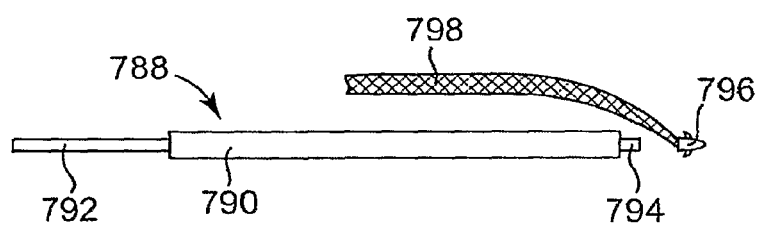
FIGS. 37-38 illustrate another insertion tool for placing an implant.

FIG. 37 illustrates insertion tool 788 for securing a pelvic implant at tissue of the pelvic region, such as at deep pelvic tissue at or near the arcus tendineus, sacrospinous ligament, coccygeous muscle, iliococcygeous muscle, levator ani muscle, or in a region of the ischial spine. Tool 788 includes a handle (not shown) that functionally connects to cannula 790, and (separately) to memory shape wire 792, which is slidable located within cannula 790.

Shape-memory wire 792 has a first form ("natural shape") and is bendable to a second form. The first form may be a form that, when attached to a distal end of an extension portion, and extended from an end of cannula 790, can facilitate placement of the distal end at tissue in the pelvic region. The first form can be different from the shape of cannula 790; cannula 790 may be straight or curved in two or three dimensions.

In use, a distal end of wire 792 can be located within a distal end of cannula 790, where the distal end of wire 792 will bend to conform to the straight or curved form of the distal end of cannula 790. The distal end of wire 792 can then be extended from the distal end of cannula 790 and can be allowed to take a natural shape that can be curved in one or two dimensions. The material of wire 792 should be strong enough to be useful to function as a portion of an insertion tool useful in a surgical procedure as described. One example of such a shape-memory material is a material known as Nitinol, which is a generic trade name for NiTi alloys that include the materials Nickel (Ni) Titanium (Ti). Advantageously, any of these materials can have a fatigue resistance that is orders of magnitude higher than that of any linearly elastic material.

Figure 38:
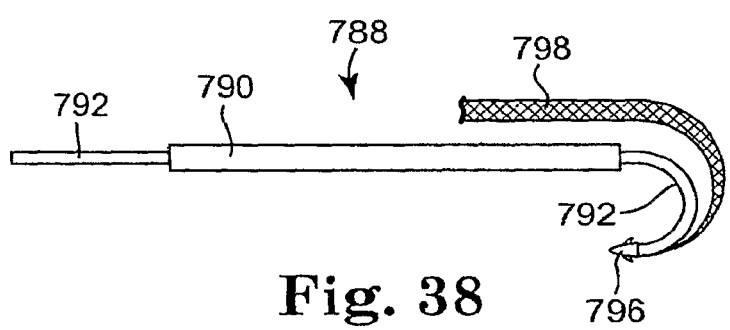

As illustrated in FIG. 38, insertion tool 788 can be used to position self-fixating tip 796 at a desired location in the pelvic region, such as at or (e.g., around) the arcus tendineus (not shown). Cannula 790 can be attached to a handle (not shown) at a proximal end of tool 788, and wire 792 can be moved (e.g., slid) lengthwise within cannula 790, such as by a control mechanism located at the handle. As wire 792 is pushed through the cannula 790, a distal end of wire 792 extends from a distal end of cannula 790 and follows a curved path defined by the shape memory (i.e., takes on a "natural shape"). Wire 792 can be given a two- or three-dimensionally curved natural shape so that when extended out of the distal end of cannula 790, wire 792 produces a two- or three-dimensionally curved tissue path as shown in FIG. 38. Self-fixating tip 796 of implant 798 can be pushed through the tissue path (e.g., that rotates around arcus tendineus), and implanted in tissue behind the arcus tendineus.

Figure 39:
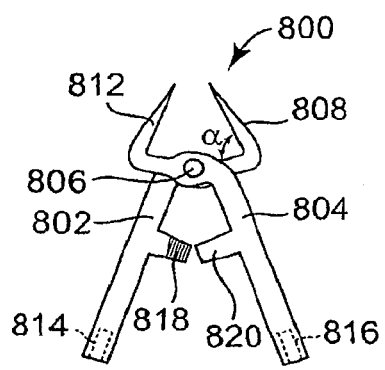
FIG. 39 illustrates a tissue clamp according to the invention in an open or unlocked configuration.

FIG. 39 shows another form of tissue fastener, a tissue clamp (800), useful according to the present description to secure a distal end of an extension portion at tissue in the pelvic region. A tissue clamp may be useful to attach a distal end of an extension portion to tissue that may not be amenable to insertion of a self-fixating tip or "soft-tissue anchor." For example, tissue in a region of the ischial spine may be more shallow than other tissue in the pelvic region, and may allow attachment of a tissue clamp more readily than insertion of a soft-tissue anchor.

Figure 40:
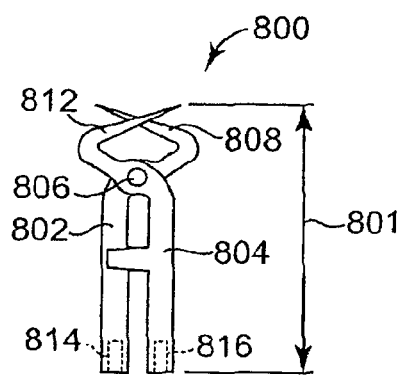
FIG. 40 illustrates the tissue clamp of FIG. 36 in a closed or locked configuration.
Figure 41:
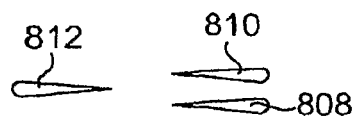
FIG. 41 illustrates a top schematic view of the open configuration of the tissue clamp of FIG. 39.
Figure 42:
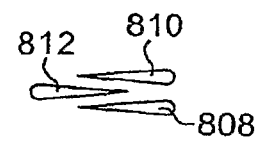
FIG. 42 illustrates a top schematic view of the closed configuration of the tissue clamp of FIG. 40.

Referring to FIG. 39, tissue clamp 800 is shown in an open or unlocked configuration. FIG. 40 shows tissue clamp 800 in a closed or locked configuration. FIGS. 41 and 42 show schematic top views of the open and closed configurations.

Tissue clamp 800 can be used to secure an end of an end of an extension portion to tissue of the pelvic region, such as a ligament, tendon, muscle, fascia, e.g., at a region of the ischial spine, such as to tissue that is relatively less amenable to attachment by use of a soft tissue anchor. Generally, tissue clamp 800 includes moveable arms or jaws that include multiple teeth that can penetrate tissue, after which the arms or jaws can be closed and optionally locked to secure tissue clamp 800 to the tissue.

As referred to herein, the term "tissue clamp" refers to a clamp such as clamp 800, useful for attachment to tissue of the pelvic region. As illustrated, tissue clamp 800 includes first and second clamp arms 802 and 804 pivotably connected at pivot 806. First clamp arm 802 includes teeth 808 and 810 that are able to grip tissue when tissue clamp 800 is installed. Second clamp arm 804 includes tooth 812 that nests between teeth 808 and 810 in the closed configuration as shown in FIG. 42. Additional teeth may be used with either clamp arm.

A clamp such as clamp 800 may be prepared from any suitable material, such as a surgical metal, ceramic, or a plastic that is sufficiently rigid and strong to be useful in this type of application.

Tissue clamp 800 can be secured at a distal end of an extension portion by any fastening mode. As illustrated, first and second clamp arms 802 and 804 also include apertures 814 and 816, either or both of which can be used to attach clamp 800 to a distal end of an extension portion of a pelvic implant (not shown). Other modes of attachment can also be used such as adhesive, a metal crimp, etc.

First and second clamp arms 802 and 804 also include optional locking tabs 818 and 820 that function to lock clamp arms 802 and 804 in the closed position when installed. Each locking tab 818 and 820 includes at least one locking tooth engagement that cooperates with an opposing structure (e.g., locking tooth, ridge, etc.) to lock tissue clamp 800 in the closed configuration similar to a hemostat.

Dimensions of a tissue clamp can be any useful size, and may relatively small, e.g., of the same range as dimensions of a self-fixating tip. In an exemplary embodiment of tissue clamp 800, the overall length 801 of tissue clamp 800 in the closed configuration can be about one centimeter, e.g., from about 0.5 to about 1.2 centimeter. Also, in the closed configuration, the distance from pivot 806 to an end or tip of a jaw (measured along a longitudinal axis parallel to line 801) may be about three millimeters, e.g., from about 2 to about 6 millimeters. Preferably, the angle between a jaw and a tooth, α, can be about thirty degrees, e.g., from about 20 to about 50 degrees.

In use, areas for attachment of a tissue clamp such as tissue clamp 800 can include the obturator internus muscle, coccygeous muscle, iliococcygeous muscle, levator ani muscle, puborectalis muscle, a region of the ischial spine, the levator ani, the sacrospinous ligament, and the tendinous arch of the levator ani muscle for treating vaginal prolapse, urinary stress incontinence, and fecal incontinence.

Figure 43:
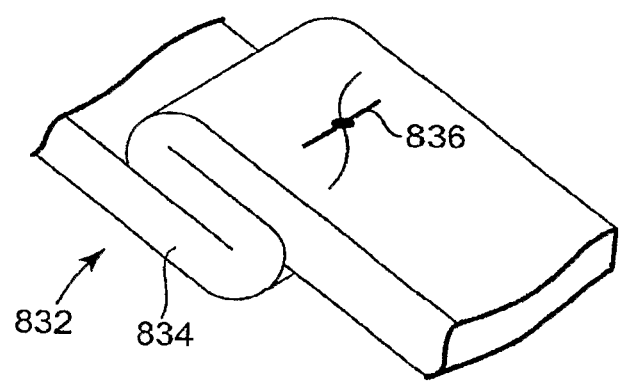
FIG. 43 illustrates an extension portion that can be used with a pelvic implant according to the invention.

FIG. 43 illustrates extension portion 832, which can be used with a pelvic implant according to the present description. Extension portion 832 may optionally be part of an extension portion piece, or part of a support portion piece arm of a multi-piece implant. Extension portion 832 includes biocompatible mesh material and one or more releasable mesh folds 834 (only one is illustrated), each secured by a suture 836. In use, one or more of sutures 836 can be cut to release one or more folds to lengthen extension portion 832, as desired. A mesh fold can be used in combination with other types of adjustable extension portions described herein (e.g., that involve a frictional adjusting element) by placing an implant as desired and adjusting a length of an extension portion by cutting a suture 836 to release a fold 834, which lengthens the extension portion.

Figure 44:
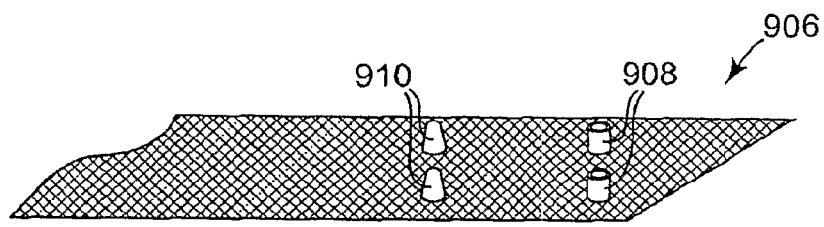
FIGS. 44 and 44A illustrate exemplary implants according to the invention.
Figure 46:
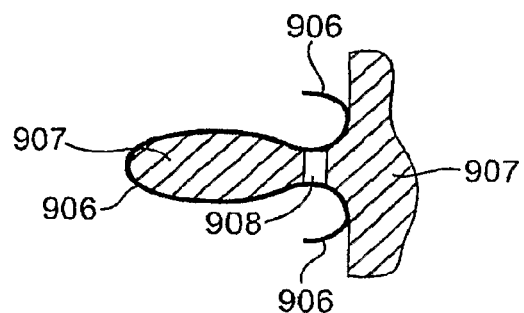
FIG. 46 illustrates the implant of FIG. 44 as implanted into tissue.

FIG. 44 shows implant 906 that includes a tissue fastener for placing a distal end of an extension portion at tissue of the pelvic region. Implant 906 includes plural (only one is required) male connector elements 910 and plural (only one is required) female connector elements 908 that are opposed and that can be connected to securely engage each other through soft tissue, e.g., muscle or fascia in the pelvic region, as shown in FIG. 46.

Figure 44A:
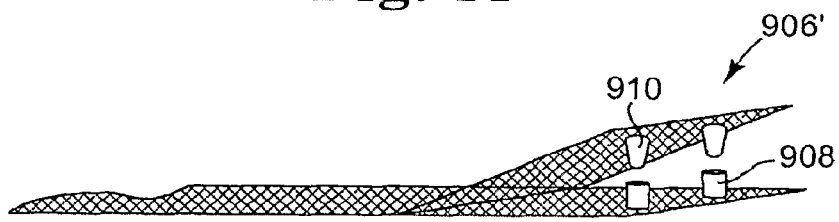

FIG. 44A shows another embodiment of implant, implant 906', that includes a tissue fastener for placing a distal end of an extension portion at tissue of the pelvic region. Implant 906' includes plural (only one is required) male connector elements 910 and plural (only one is required) female connector elements 908 that are opposed and that can be connected to securely engage each other through soft tissue, e.g., muscle or fascia in the pelvic region, as shown in FIG. 46. Implant 906' includes a secondary extension 907 that extends from main extension portion 909. Each of secondary extension 907 and main extension portion 909 include a female or male connector element.

Generally, a male frictional adjusting element (e.g., 910) can be inserted into an opposing female frictional adjusting element (e.g., 908), and surfaces of the two opposing connector elements prevent the male and female connector elements from separating. Any cooperatively engaging female and male connector elements can be used, such as those that include grooves, ridges, holes, flanges, hooks, and the like, that frictionally engage to securely hold the female connector element to the male connector element when the two are engaged. The opposing female and male connector elements must also be capable of penetrating tissue such as muscle or fascia in a manner that allows the male element to engage the female element when the two are pushed together with tissue placed between the male and female elements.

Figure 45:
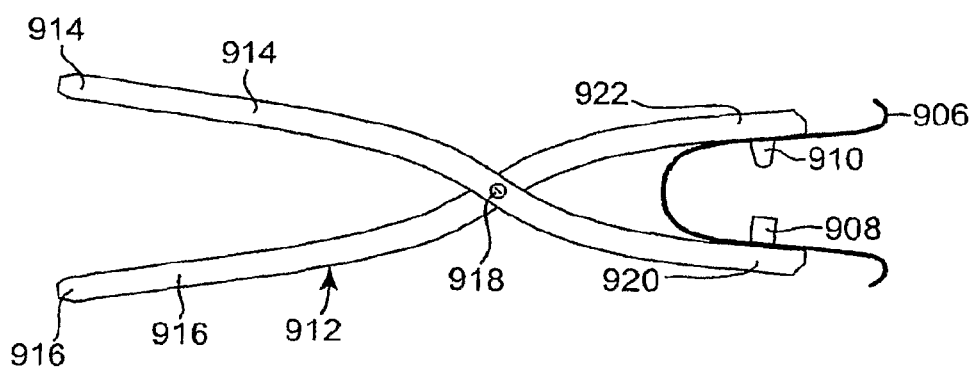
FIG. 45 illustrates an insertion tool for installing the implants shown in FIGS. 44 and 44A.

FIG. 45 illustrates an installation tool, tool 912, for installing implant 906 or 906'. Installation tool 912 includes tool arms 914 and 916 that pivot about pivot point 918. Tool arms 914 and 916 include jaws 920 and 922, respectively. Jaws 920 and 922 include structure to engage male and female connector elements 908 and 910 to hold elements 908 and 910 for placing in tissue. Jaws 920 and 922 are positioned at a desired tissue location, with a piece of tissue placed (or pinched") between male and female connector elements 910 and 908. Tool 912 is then used to drive male connector element 910 toward female connector element 908, through tissue, toward each other, and into engagement within each other to hold a distal end of an extension portion of implant 906 to pelvic tissue at a selected tissue location. Such action will bite or clamp a portion of tissue between the implant 906 for securing implant 906 in position.

FIG. 45 shows and insertion tool 912, holding male and female connector elements 910 and 908, for placement within tissue.

FIG. 46 shows male and female connector elements 910 and 908, connected to each other with within tissue 907, to connect implant 907 to tissue 907.

Figure 47:
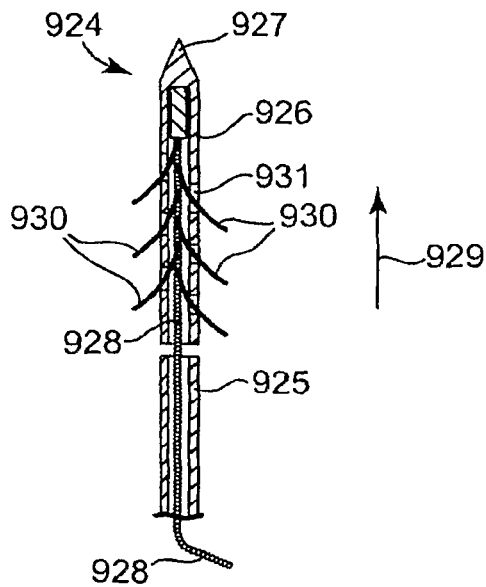
FIGS. 47 through 50 illustrate exemplary tissue fasteners and associated insertion tools according to the invention.

FIG. 47 shows an embodiment of tissue fastener, self-fixating tip 924, that can be used in combination with an implant or extension portion. Self-fixating tip 924 can be connected to a pelvic implant (not shown), such as at a distal end of an extension portion, and used to secure the distal end to tissue in the pelvic region. Self-fixating tip 924 includes housing portion 926 having tip 927 and wire 928 connected to deployable barbs 930 that pass through apertures 931 in housing portion 926. Self-fixating tip 924 can be designed so barbs 930 deploy by moving wire 928 relative to housing portion 926.

Barbs 930 may be designed to deploy upon advancement in direction 929, such as by a spring force of the barb material. That is, barbs 930 may be held within housing portion 929 until barbs 930 advance to apertures 931 and then deploy by the spring force.

In an alternate embodiment, barbs 930 can be designed to deploy upon translation of wire 928 in a direction opposite direction 929. According to this design, barbs 930 can be pre-positioned or staged near apertures 931 so that a curvature of barbs 930 causes barbs 930 to deploy through apertures 931 upon translation of wire 928.

In use, insertion tool 925 is releasable coupled to self-fixating tip 924. Any disconnectable coupling can be used such as those include that include a thread, flange, detent, spring, shoulder, etc. Insertion tool 925 is used to advance self-fixating tip 924 into a desired location in tissue. When positioned as desired, barbs 930 can be deployed (i.e., extended from housing portion 929) to secure self-fixating tip 924 to tissue. Insertion tool 925 is then decoupled from the self-fixating tip 924 and removed.

Figure 48:
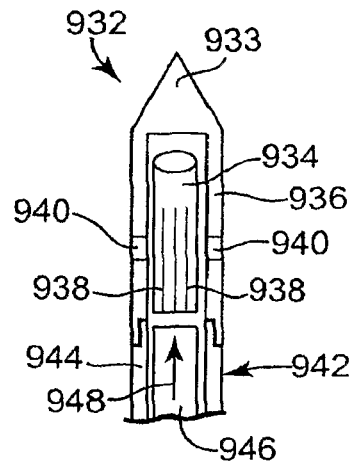
Figure 49:
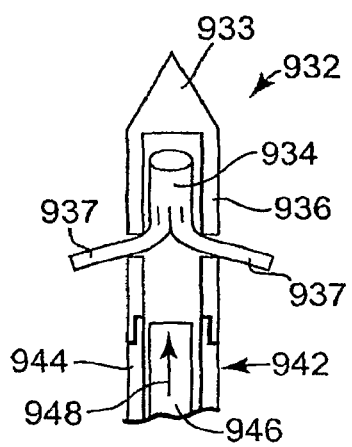

FIGS. 47-49 show another embodiment of a tissue fastener, self-fixating tip 932, along with installation tool 942. Self-fixating tip 932 can be connected to a pelvic implant (not shown) and used for securing the pelvic implant to tissue in the pelvic region. As shown, self-fixating tip 932 includes tube portion 934 positioned within housing 936. Housing 936 includes tip 933 and apertures 940. Tube portion 934 includes slits 938 that define spring-loaded barbs 937 that can flare outward to extend through apertures 940 when advanced by the installation tool 934.

Installation tool 942 includes cannula 944 and rod 946 that can be translated relative to and within cannula 946 along deployment direction 948. Installation tool 934 also includes shoulder 950 that mates with shoulder 952 of housing 936 of self-fixating tip 932. Other connections can be used to couple and decouple installation tool 934 and self-fixating tip 932 such as those that include threads, flanges, shoulders, detents, springs, and the like.

Figure 50:
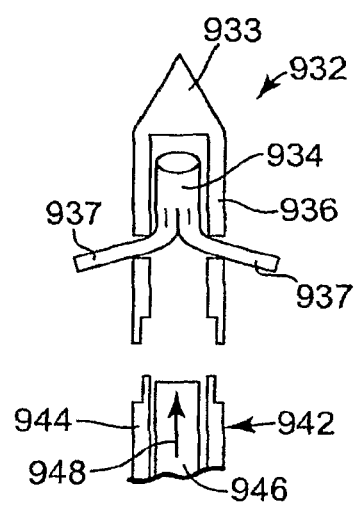

In use, insertion tool 934 is coupled to self-fixating tip 932. Insertion tool 934 is then used to advance self-fixating tip 932 to a desired location in tissue. When positioned as desired, rod 946 is advanced along direction 948 to drive tube 934 in one or more directions to position barbs 937 to deploy through apertures 940, and extend into tissue, to secure self-fixating tip 932 to tissue (see FIG. 49). Insertion tool 934 is then decoupled from self-fixating tip 932 and removed (see FIG. 50).

Any of the above general and detailed descriptions of features of implants, insertion tools, tissue fasteners, and methods, etc., can be used in any desired combination, for treating female or male pelvic conditions.

Although the invention has been described in terms of particular embodiments and applications, one of ordinary skill in the art, in light of this teaching, can generate additional embodiments and modifications without departing from the spirit of or exceeding the scope of the claimed invention.

Accordingly, it is to be understood that the drawings and descriptions herein are proffered by way of example to facilitate comprehension of the invention and should not be construed to limit the scope thereof.

What is claimed is:

1. A multi-piece pelvic implant comprising a tissue support portion, a first extension portion, and a second extension portion, the implant comprising pieces that include:
   a support portion piece comprising the tissue support portion,
   the first extension portion comprising a first extension portion piece, and
   the second extension portion comprising a second extension portion piece,
   wherein the first extension portion piece is adjustably connected to the support portion piece, and the implant includes a first frictional adjusting element that allows adjustment of a length of the first extension portion, the first frictional adjusting element comprising a first aperture through which a segment of the first extension portion extends and a surface that frictionally engages the segment of the first extension portion, wherein the first frictional adjusting element preferentially allows movement of the segment of the first extension portion through the aperture in one direction and inhibits movement of the segment of the first extension portion in an opposing direction,
   wherein the second extension portion piece is adjustably connected to the support portion piece, and the implant includes a second frictional adjusting element that allows adjustment of a length of the second extension portion, the second frictional adjusting element comprising a second aperture through which a segment of the second extension portion extends and a surface that frictionally engages the segment of the second extension portion, wherein the second frictional adjusting element preferentially allows movement of the segment of the second extension portion through the second aperture in one direction and inhibits movement of the segment of the second extension portion in an opposing direction,
   wherein the first frictional adjusting element comprises a grommet and the second frictional adjusting element comprises a grommet.

2. The implant of claim 1 wherein the first frictional adjusting element is secured to the implant at a location selected from the tissue support portion of the support portion piece, a support portion piece arm, and the first extension portion piece, and wherein the second frictional adjusting element is secured to the implant at a location selected from the tissue support portion of the support portion piece, a support portion piece arm, and the second extension portion piece.

3. The implant of claim 2 wherein the first and second frictional adjusting elements are secured to a proximal end of the first and second extension portion pieces.

4. The implant of claim 1 wherein the support portion piece comprises
   the tissue support portion,
   at least two support portion piece arms extending from the tissue support portion, and
   the first and the second frictional adjusting elements secured to the support portion piece arms.

5. The implant of claim 1 wherein
   the first frictional adjusting element is secured to a proximal end of the first extension portion piece,
   a tissue fastener is attached at a distal end of the first extension portion piece, and the support portion piece comprises an elongate support portion piece arm extending through the first frictional adjusting element aperture.

6. The implant according to claim 1 comprising the tissue support portion and four extension portions including two superior extension portions of fixed length and two inferior extension portions of adjustable length.

7. The implant of claim 1, wherein the grommet of the first frictional adjusting element is located at the first extension portion piece, and the grommet of the second frictional adjusting element is located at the second extension portion piece.

8. The implant of claim 1, wherein the grommet of the first frictional adjusting element is secured to the support portion piece, and the grommet of the second frictional adjusting element is secured to the support portion piece.

9. In combination, the pelvic implant according to claim 1 and an adjusting tool, the adjusting tool comprising an elongate shaft and a distal end, the distal end being capable of engaging the grommet of the first frictional adjusting element to move the grommet of the first adjusting element along a length of the segment of the first extension portion.

* * * * *